United States Patent
Tatkov et al.

(10) Patent No.: US 10,058,663 B2
(45) Date of Patent: Aug. 28, 2018

(54) CONTROL OF HUMIDIFIER CHAMBER TEMPERATURE FOR ACCURATE HUMIDITY CONTROL

(71) Applicant: FISHER & PAYKEL HEATHCARE LIMITED, Auckland (NZ)

(72) Inventors: Stanislav Tatkov, Howick Auckland (NZ); Christopher Malcolm Crone, Auckland (NZ); Peter Hawkins, Greenlane Auckland (NZ); Jae Chul Han, St. Heliers Auckland (NZ); Kevin Peter O'Donnell, Eastern Beach Auckland (NZ); Andrew Robert Donald Somervell, Onehunga Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 542 days.

(21) Appl. No.: 14/092,488

(22) Filed: Nov. 27, 2013

(65) Prior Publication Data

US 2014/0166005 A1 Jun. 19, 2014

Related U.S. Application Data

(63) Continuation of application No. 12/995,458, filed as application No. PCT/NZ2009/000091 on May 27, 2009, now Pat. No. 8,616,202.

(Continued)

(51) Int. Cl.
*A61M 16/08* (2006.01)
*A61M 16/16* (2006.01)
(Continued)

(52) U.S. Cl.
CPC .... *A61M 16/0051* (2013.01); *A61M 16/0012* (2014.02); *A61M 16/0069* (2014.02);
(Continued)

(58) Field of Classification Search
CPC ............ A61M 16/0051; A61M 16/161; A61M 16/0057; A61M 16/0875; A61M 16/10;
(Continued)

(56) References Cited

U.S. PATENT DOCUMENTS 4,621,632 A * 11/1986 Bartels ............... A61M 16/1075
128/203.17
5,164,652 A   11/1992 Johnson et al.
(Continued)

FOREIGN PATENT DOCUMENTS

CN         1204266      1/1999
DE       103 12 881     5/2004
(Continued)

OTHER PUBLICATIONS

Melikov, A. K. et al. "Accuracy Limitations for Low Velocity Measurements and Draft Assessment Rooms" *HVAC & R Research* 13(6), Nov. 2007.

(Continued)

*Primary Examiner* — Kathryn E Ditmer
(74) *Attorney, Agent, or Firm* — Knobbe, Martens, Olson & Bear, LLP

(57) ABSTRACT

A breathing assistance system is provided for delivering a stream flow of heated, humidified gases to a user. The system includes a humidifier unit which holds and heats a volume of water, and which in use receives a flow of gases from a gases source via an inlet port. The flow of gases passes through the humidifier and exits via an exit port. The system further includes a temperature sensor which measures the temperature of the gases exiting the humidifier (Continued)

unit, an ambient temperature sensor which measures the temperature of gases before they enter the humidifier unit, and a flow sensor which measures the flow rate of the gases stream. The system also includes a controller which receives data from the temperature and flow sensors, and which determines a control output in response. The control output is configured to adjust the power to the humidifier unit to achieve a desired output at the humidifier unit exit port.

21 Claims, 15 Drawing Sheets

Related U.S. Application Data

(60) Provisional application No. 61/056,335, filed on May 27, 2008.

(51) Int. Cl.
| | |
|---|---|
| A61M 16/00 | (2006.01) |
| A61M 16/10 | (2006.01) |
| A61M 16/04 | (2006.01) |
| A61M 16/06 | (2006.01) |

(52) U.S. Cl.
CPC ...... A61M 16/026 (2017.08); A61M 16/0465 (2013.01); A61M 16/0666 (2013.01); A61M 16/0875 (2013.01); A61M 16/109 (2014.02); A61M 16/1075 (2013.01); A61M 16/1095 (2014.02); A61M 16/16 (2013.01); A61M 16/161 (2014.02); A61M 16/0841 (2014.02); A61M 2205/3368 (2013.01)

(58) Field of Classification Search
CPC ............ A61M 16/1075; A61M 16/108; A61M 16/1085; A61M 16/109; A61M 16/1095; A61M 16/16; F24F 6/00; F24F 6/025
See application file for complete search history.

(56) References Cited

U.S. PATENT DOCUMENTS

| | | | |
|---|---|---|---|
| 5,347,211 A | | 9/1994 | Jakubowski |
| 5,428,752 A | | 6/1995 | Goren et al. |
| 5,449,234 A | | 9/1995 | Gipp et al. |
| 5,558,084 A | * | 9/1996 | Daniell ............ A61M 16/1075 128/203.12 |
| 5,664,563 A | * | 9/1997 | Schroeder ......... A61M 16/0078 128/204.24 |
| 5,862,802 A | | 1/1999 | Bird |
| 6,038,457 A | | 3/2000 | Barkat |
| 6,078,730 A | | 6/2000 | Huddart et al. |
| 6,272,933 B1 | | 8/2001 | Gradon et al. |
| 6,384,755 B1 | | 5/2002 | Hayden |
| 6,584,972 B2 | | 7/2003 | McPhee |
| 6,594,366 B1 | | 7/2003 | Adams |
| 6,668,828 B1 | | 12/2003 | Figley et al. |
| 6,895,803 B2 | | 5/2005 | Seakins et al. |
| 7,111,624 B2 | | 9/2006 | Thurdor et al. |
| 7,802,569 B2 | | 9/2010 | Yeates et al. |
| 7,962,018 B2 | | 6/2011 | Hunt et al. |
| 8,616,202 B2 | | 12/2013 | Tatkov et al. |
| 2001/0017134 A1 | | 8/2001 | Bahr |
| 2002/0129815 A1 | * | 9/2002 | McPhee .............. A61M 16/161 128/200.24 |
| 2003/0236015 A1 | | 12/2003 | Edirisuriya et al. |
| 2004/0182386 A1 | * | 9/2004 | Meier .................. A61M 16/16 128/203.12 |
| 2004/0221844 A1 | * | 11/2004 | Hunt .................. A61M 16/161 128/204.17 |
| 2006/0027234 A1 | | 2/2006 | Gradon et al. |
| 2006/0113690 A1 | * | 6/2006 | Huddart ............ A61M 16/1075 261/129 |
| 2007/0125376 A1 | * | 6/2007 | Reinstadtler ...... A61M 16/1075 128/203.26 |
| 2008/0028850 A1 | | 2/2008 | Payton et al. |
| 2008/0196722 A1 | | 2/2008 | Kramer et al. |
| 2008/0072903 A1 | * | 3/2008 | Roth .................... A61M 16/08 128/204.22 |
| 2008/0190427 A1 | | 5/2008 | Payton et al. |
| 2008/0190426 A1 | * | 8/2008 | Koch .................... A61M 16/16 128/203.16 |
| 2008/0308100 A1 | * | 12/2008 | Pujol ................. A61M 16/1075 128/203.14 |
| 2008/0310994 A1 | | 12/2008 | O'Donnell et al. |
| 2009/0071478 A1 | | 3/2009 | Kalfon |
| 2009/0250055 A1 | * | 10/2009 | Radomski ............ A61M 16/16 128/203.14 |
| 2010/0132707 A1 | * | 6/2010 | Muller ............... A61M 16/1075 128/204.17 |
| 2012/0048271 A1 | | 3/2012 | O'Donnell et al. |

FOREIGN PATENT DOCUMENTS

| | | | |
|---|---|---|---|
| DE | 102007015038 | | 3/2008 |
| EP | 1 647 297 A2 | | 4/2006 |
| GB | 1 448 473 | | 9/1976 |
| GB | 2 173 274 | | 10/1986 |
| JP | 2003-509134 | | 3/2003 |
| JP | 2005-537083 | | 12/2005 |
| WO | WO 2001/013981 A1 | | 1/2001 |
| WO | WO 01/19440 | | 3/2001 |
| WO | WO 2004/020031 | | 3/2004 |
| WO | WO 2004/112873 A1 | | 12/2004 |
| WO | WO 2006/126900 | | 11/2006 |
| WO | WO 2007121736 A2 | * | 11/2007 ........ A61M 16/1075 |
| WO | WO2008/052364 A1 | | 8/2008 |

OTHER PUBLICATIONS

International Search Report dated Oct. 16, 2009 in the PCT International Application No. PCT/NZ2009/000091 in 5 pages.
Written Opinion of the International Search Authority dated Oct. 16, 2009 in the PCT International Application No. PCT/NZ2009/000091 in 5 pages.
Australian Patent Examination Report No. 1 for Patent Application No. 2009251939 dated May 30, 2014 in 3 pages.
Supplementary European Search Report for European Application No. EP 09 75 5102 dated Jun. 17, 2014 in 7 pages.
Declaration of Andrew Bath, U.S. Pat. No. 8,186,345, IPR No. 2016-01723.
Declaration of Andrew Bath, U.S. Pat. No. 8,453,641, IPR No. 2016-01724.
Declaration of Andrew Bath, U.S. Pat. No. 9,265,902, IPR No. 2016-01735.
File History of U.S. Pat. No. 8,453,641 to Matthew Jon Payton et al.
Fisher & Paykel Healthcare, Annual Report 2003, accessed from https://www.fphcare.co.nz/files/documents/investorannouncements/.
Fisher & Paykel Healthcare, FY04 Full Year Overview & Update, May 24, 2004, dated on https://www.fphcare.com/investor/presentations/presentations-2004/ , accessed from https://www.fphcare.com/CMSPages/GetFile.aspx?guid=50c66a57-cb04-4e4d-b220-92e371d07292.
Fisher & Paykel Healthcare, Full Year Analyst Briefing, Jun. 5, 2002, dated on https://www.fphcare.com/investor/presentations/presentations-2002/ , accessed from https://www.fphcare.com/CMSPages/GetFile.aspx?guid=ef7b02d1-cc43-4d62-a1f7-494be1bbb2dc.
Fisher & Paykel MR810 Manual, Rev. C.
MR850 Respiratory Humidifier Instruction Sheet, Rev. G, Feb. 2004.
Patent Owner's Complaint for *Fisher & Paykel Healthcare Ltd.* v. *ResMed Corp.*, Case No. 3:16-cv-02068-GPC-WVG (S.D. Cal.).

(56) References Cited

OTHER PUBLICATIONS

Patent Owner's Complaint for *Fisher & Paykel Healthcare Ltd.* v. *ResMed Corp.*, Case No. 2:16-cv-06099-R-AJW (C.D. Cal.).
Patent Owner's Notice of Voluntary Dismissal Without Prejudice for *Fisher & Paykel Healthcare Ltd.* v. *ResMed Corp.*, Case No. 2:16- cv-06099-R-AJW (C.D. Cal.).
Petitioners' Complaint for *ResMed Inc., et al.* v. *Fisher & Paykel Healthcare Corp. Ltd.*, et al., Case No. 3:16-cv-02072-JAH-MDD (S.D. Cal.).
Petitioners' Notice of Voluntary Dismissal Without Prejudice for *ResMed Inc., et al.* v. *Fisher & Paykel Healthcare Corp. Ltd., et al.*, Case No. 3:16-cv-02072-JAH-MDD (S.D. Cal.).
Petition for Inter Partes Review of U.S. Pat. No. 8,186,345, IPR No. 2016-01723 filed on Sep. 7, 2016.
Patent Owner Preliminary Response for U.S. Pat. No. 8,186,345, IPR No. 2016-01723 filed on Dec. 13, 2016.
Petition for Inter Partes Review of U.S. Pat. No. 8,453,641, IPR No. 2016-01724 filed on Sep. 7, 2016.
Corrected Petition for Inter Partes Review of U.S. Pat. No. 8,453,641, IPR No. 2016-01724 filed on Jan. 26, 2017.
Patent Owner Preliminary Response for U.S. Pat. No. 8,453,641, IPR No. 2016-01724 filed on Dec. 16, 2016.
Patent Owner Preliminary Response to Corrected Petition for U.S. Pat. No. 8,453,641, IPR No. 2016-01724 filed on Jan. 27, 2017.
Petition for Inter Partes Review of U.S. Pat. No. 9,265,902, IPR No. 2016-01735 filed on Sep. 7, 2016.
Corrected Petition for Inter Partes Review of U.S. Pat. No. 9,265,902, IPR No. 2016-01735 filed on Jan. 26, 2017.
Patent Owner Preliminary Response for U.S. Pat. No. 9,265,902, IPR No. 2016-01735 filed on Dec. 13, 2016.
Patent Owner Preliminary Response to Corrected Petition for U.S. Pat. No. 9,265,902, IPR No. 2016-01735 filed on Jan. 27, 2017.
Final Written Decision, U.S. Pat. No. 9,265,902, IPR No. 2016-01735 dated Mar. 7, 2018.
Final Written Decision, U.S. Pat. No. 8,453,641, IPR No. 2016-01724 dated Mar. 7, 2018.
Oct. 5, 2017 Andrew Bath Deposition Transcript, U.S. Pat. No. 8,453,641, IPR No. 2016-01724.
Oct. 5, 2017 Andrew Bath Deposition Transcript, U.S. Pat. No. 9,265,902, IPR No. 2016-01735.
Authoritative Dictionary of IEEE Standards (2000), filed on Dec. 13, 2016.
Crash Course in Electronics Technology, filed on Aug. 24, 2017.
Darby Declaration, U.S. Pat. No. 8,453,641, IPR No. 2016-01724, filed on Jun. 1, 2017.
Darby Declaration, U.S. Pat. No. 9,265,902, IPR No. 2016-01735, filed on Jun. 1, 2017.
Decision—Denying Institution of Inter Partes Review, U.S. Pat. No. 8,186,345, IPR No. 2016-01723, filed on Mar. 9, 2017.
Deposition Transcript of Patent Owners Declarant, Adam Darby, dated Aug. 9, 2017, U.S. Pat. No. 8,453,641, IPR No. 2016-01724.
Deposition Transcript of Patent Owners Declarant, Adam Darby, dated Aug. 9, 2017, U.S. Pat. No. 9,265,902, IPR No. 2016-01735.
Deposition Transcript of Patent Owners Declarant, Adam Darby, dated Oct. 17, 2017, U.S. Pat. No. 8,453,641, IPR No. 2016-01724.
Deposition Transcript of Patent Owners Declarant, Adam Darby, dated Oct. 17, 2017, U.S. Pat. No. 9,265,902, IPR No. 2016-01735.
Elementary Linear Circuit Analysis, filed on Aug. 24, 2017.
FDT86256L N-Channel PowerTrench MOSFET Datasheet, filed on Oct. 10, 2017.
Hearing Transcript, U.S. Pat. No. 8,453,641, IPR No. 2016-01724, filed on Nov. 17, 2017.
Hearing Transcript, U.S. Pat. No. 9,265,902, IPR No. 2016-01735, filed on Nov. 17, 2017.
Introduction to Logic Design, filed on Aug. 24, 2017.
Khandpur, Printed Circuit Boards (2006), filed on Dec. 13, 2016.
Newnes Electronics Toolkit, filed on Aug. 24, 2017.
NTC Thermistors—Accuracy Line Datasheet, filed on Aug. 24, 2017.

Microchip Technology AN685 Application Note, filed on Oct. 10, 2017.
Patent Owner Motion for Observations on Cross-Examination Testimony of Andrew Bath, U.S. Pat. No. 8,453,641, IPR No. 2016-01724, filed on Oct. 20, 2017.
Patent Owner Motion for Observations on Cross-Examination Testimony of Andrew Bath, U.S. Pat. No. 9,265,902, IPR No. 2016-01735, filed on Oct. 20, 2017.
Patent Owner Motion to Exclude Evidence, U.S. Pat. No. 8,453,641, IPR No. 2016-01724, filed on Oct. 20, 2017.
Patent Owner Motion to Exclude Evidence, U.S. Pat. No. 9,265,902, IPR No. 2016-01735, filed on Oct. 20, 2017.
Patent Owner Opposition to Petitioner Motion to Exclude Evidence, U.S. Pat. No. 8,453,641, IPR No. 2016-01724, filed on Oct. 26, 2017.
Patent Owner Opposition to Petitioners Motion to Exclude Evidence, U.S. Pat. No. 9,265,902, IPR No. 2016-01735, filed on Oct. 26, 2017.
Patent Owner Response to Corrected Petition, U.S. Pat. No. 8,453,641, IPR No. 2016-01724, filed on Jun. 1, 2017.
Patent Owner Response to Corrected Petition, U.S. Pat. No. 9,265,902, IPR No. 2016-01735, filed on Jun. 1, 2017.
Patent Owner Response to Motion for Observations, U.S. Pat. No. 8,453,641, IPR No. 2016-01724, filed on Oct. 26, 2017.
Patent Owner Response to Motion for Observations, U.S. Pat. No. 9,265,902, IPR No. 2016-01735, filed on Oct. 26, 2017.
Patent Owner's Sur-Reply in Response to Petitioners' Reply, U.S. Pat. No. 8,453,641, IPR No. 2016-01724, filed on Oct. 10, 2017.
Patent Owner's Sur-Reply in Response to Petitioner's Reply, U.S. Pat. No. 9,265,902, IPR No. 2016-01735, filed on Oct. 10, 2017.
Petitioner's Motion for Observation, U.S. Pat. No. 8,453,641, IPR No. 2016-01724, filed on Oct. 20, 2017.
Petitioner's Motion for Observation, U.S. Pat. No. 9,265,902, IPR No. 2016-01735, filed on Oct. 20, 2017.
Petitioner's Motion to Exclude, U.S. Pat. No. 9,265,902, IPR No. 2016-01735, filed on Oct. 20, 2017.
Petitioner's Motion to Exclude Evidence, U.S. Pat. No. 8,453,641, IPR No. 2016-01724, filed on Oct. 20, 2017.
Petitioner's Opposition to Motion to Exclude, U.S. Pat. No. 8,453,641, IPR No. 2016-01724, filed on Oct. 26, 2017.
Petitioner's Opposition to Motion to Exclude, U.S. Pat. No. 9,265,902, IPR No. 2016-01735, filed on Oct. 26, 2017.
Petitioner's Reply to Patent Owner's Opposition to Petitioner's Motion to Exclude Evidence, U.S. Pat. No. 8,453,641, IPR No. 2016-01724, filed on Nov. 2, 2017.
Petitioner's Reply to Patent Owner's Opposition to Petitioner's Motion to Exclude Evidence, U.S. Pat. No. 9,265,902, IPR No. 2016-01735, filed on Nov. 2, 2017.
Petitioner's Reply to Patent Owner's Response, U.S. Pat. No. 8,453,641, IPR No. 2016-01724, filed on Aug. 24, 2017.
Petitioner's Reply to Patent Owner's Response to Petition, U.S. Pat. No. 9,265,902, IPR No. 2016-01735, filed on Aug. 24, 2017.
Petitioner's Response to Motion for Observation, U.S. Pat. No. 8,453,641, IPR No. 2016-01724, filed on Oct. 26, 2017.
Petitioner's Response to Motion for Observation, U.S. Pat. No. 9,265,902, IPR No. 2016-01735, filed on Oct. 26, 2017.
Potter, Measuring Temperature with Thermistors, filed on Jun. 1, 2017.
Reply in Support of Patent Owner Motion to Exclude Evidence, U.S. Pat. No. 8,453,641, IPR No. 2016-01724, filed on Nov. 2, 2017.
Reply in Support of Patent Owner Motion to Exclude Evidence, U.S. Pat. No. 9,265,902, IPR No. 2016-01735, filed on Nov. 2, 2017.
Second Declaration of Adam Darby, U.S. Pat. No. 8,453,641, IPR No. 2016-01724, filed on Oct. 10, 2017.
Second Declaration of Adam Darby, U.S. Pat. No. 9,265,902, IPR No. 2016-01735, filed on Oct. 10, 2017.
Second Declaration of Andrew Bath, U.S. Pat. No. 8,453,641, IPR No. 2016-01724, filed on Aug. 24, 2017.
Second Declaration of Andrew Bath, U.S. Pat. No. 9,265,902, IPR No. 2016-01735, filed on Aug. 24, 2017.
The Art of Electronics, filed on Aug. 24, 2017.

(56) References Cited

OTHER PUBLICATIONS

Trial Instituted Document, U.S. Pat. No. 8,453,641, IPR No. 2016-01724, filed on Mar. 10, 2017.
Trial Instituted Document, U.S. Pat. No. 9,265,902, IPR No. 2016-01735, filed on Mar. 10, 2017.
Vishay email correspondence with website printout, filed on Oct. 10, 2017.
Office Action issued by Indian Intellectual Property Office for Application No. 4955/KOLNP/2010 dated Mar. 3, 2018 in 8 pages.

* cited by examiner

CONTROL OF HUMIDIFIER CHAMBER TEMPERATURE FOR ACCURATE HUMIDITY CONTROL

FIELD OF THE INVENTION

This invention relates to methods and apparatus for controlling the humidity level and flow rate of gases in a device that provides a stream of heated, humidified gases to a user for therapeutic purposes. This invention particularly relates to methods and apparatus for controlling the humidity of a gases stream in devices that provide humidified air for: respiratory humidification therapy, high-flow oxygen therapy, CPAP therapy, Bi-PAP therapy, OPAP therapy, etc, or humidification of gases used for insufflation or keyhole surgery.

BACKGROUND

Devices or systems for providing a humidified gases flow to a patient for therapeutic purposes are well known in the art. Systems for providing therapy of this type (for example respiratory humidification) have a structure where gases are delivered to a humidifier chamber from a gases source. As the gases pass over the hot water, or through the heated, humidified air in the humidifier chamber, they become saturated with water vapour. The heated humidified gases are then delivered to a user or patient downstream from the humidifier chamber, via a gases conduit and a user interface. The gases delivery system can be a modular system that has been assembled from separate units, with the gases source being an assisted breathing unit or blower unit. That is, the humidifier chamber/heater and the blower unit are separate (modular) items. The modules are in use connected in series via connection conduits to allow gases to pass from the blower unit to the humidifier unit. Alternatively, the breathing assistance apparatus can be an integrated system, where the blower unit and the humidifier unit are contained within the same housing in use. In both modular and integrated systems, the gases provided by the blower unit are generally sourced from the surrounding atmosphere. A third general form of breathing assistance system, which is typically used in hospitals, is one where the breathing assistance system receives at least a portion of the gases which it uses from a central gases source, typically external to the area of use (e.g. a hospital room). A gases conduit or similar is connected between an inlet which is mounted e.g. in the wall of a patients room (or similar). The gases conduit is either connected directly to the humidifier chamber in use, or a step-down control unit or similar can be connected in series between the gases inlet and the humidifier chamber if required. This type of breathing assistance system is generally used where a patient or user may require oxygen therapy, with the oxygen supplied from the central gases source. It is common for the pure oxygen from the gases source to be blended with atmospheric air before delivery to the patient or user, for example by using a venturi located in the step-down control unit. In systems of the type where at least some of the gases are delivered from a central source, there is no need for a separate flow generator or blower—the gases are delivered from the inlet under pressure, with the step down control unit altering the pressure and flow to the required level.

An example of a known, prior art, type of modular system using atmospheric gases only is shown in FIG. 1.

In typical integrated and modular systems, the atmospheric gases are sucked in or otherwise enter a main 'blower' or assisted breathing unit, which provides a gases flow at it's outlet. The blower unit and the humidifier unit are mated with or otherwise rigidly connected to the blower unit. For example, the humidifier unit is mated to the blower unit by a slide-on or push connection, which ensures that the humidifier unit is rigidly connected to and held firmly in place on the main blower unit. An example of a system of this type is the Fisher and Paykel Healthcare 'slide-on' water chamber system shown and described in U.S. Pat. No. 7,111,624. A variation of this design is a slide-on or clip-on design where the chamber is enclosed inside a portion of the integrated unit in use. An example of this type of design is described in WO 2004/112873.

One of the problems that has been encountered with systems that provide a flow of heated, humidified gases to a patient via a gases conduit and an interface is that of adequately controlling the characteristics of the gas. Clearly, it is desirable to deliver the gas to the patient (i.e. as it exits the user interface) with the gas at precisely the right temperature, humidity, flow, and oxygen fraction (if the patient is undergoing oxygen therapy) to provide the required therapy. A therapy regime can become ineffective if the gases are not delivered to the patient with the correct or required characteristics. Often, the most desirable situation is to deliver gases that are fully saturated with water vapour (i.e. at substantially 100% relative humidity) to a user, at a constant flow rate. Other types or variations of therapy regime may call for less than 100% relative humidity. Breathing circuits are not steady-state systems, and it is difficult to ensure the gases are delivered to a user with substantially the correct characteristics. It can be difficult to achieve this result over a range of ambient temperatures, ambient humidity levels, and a range of gas flows at the point of delivery. The temperature, flow rate and humidity of a gases stream are all interdependent characteristics. When one characteristic changes, the others will also change. A number of external variables can affect the gases within a breathing circuit and make it difficult to deliver the gases to the user at substantially the right temperature, flow rate and humidity. As one example, the delivery conduit between the patient or user and the humidifier outlet is exposed to ambient atmospheric conditions, and cooling of the heated, humidified gases within the conduit can occur as the gas travels along the conduit between the exit port of the humidifier chamber and the user interface. This cooling can lead to 'rain-out' within the conduit (that is, condensate forming on the inner surface of the conduit). Rain-out is extremely undesirable for reasons that are explained in detail in WO 01/13981.

In order to assist in achieving delivery of the gases stream with the gases having the desired characteristics, prior art systems have used sensors (e.g. temperature and humidity sensors) located at various positions throughout the breathing circuit. Thermistors are generally used as temperature sensors, as these are reliable and inexpensive. Humidity sensors such as the one described in U.S. Pat. No. 6,895,803 are suitable for use with systems that deliver heated humidified gases to a user for therapeutic purposes.

In order to achieve delivery of the gases to the patient at the correct temperature and humidity, it is necessary either to measure or sense the gases characteristics at the point of delivery, or to calculate or estimate the gases characteristics at the point of delivery from measurements taken from elsewhere in the system. In order to directly measure the gases parameters at the point of delivery, sensors must be located at or close to the point of delivery—either at the end of the patient conduit or within the interface. Sensors located at or close to the point of gases delivery will give the most accurate indication of the gases state. However, one consideration when designing a breathing circuit is to ensure that the components used in the breathing circuit can be repeatedly connected and disconnected to and from each other, with high reliability. Another consideration is to keep the weight carried by the patient in use to a minimum, and therefore it is desirable to keep the number of sensors at the patient end of the conduit to a minimum, or remove the need for these altogether. It is also desirable to keep the total number of sensors in the system to a minimum, in order to reduce costs and complexity (e.g. an increased number of electrical and pneumatic connections).

In order to overcome or sidestep the problem or trade-off of accurate measurement of the gases characteristics vs complexity vs cost vs weight carried by the patient vs reliability, sensors can be located at various other points within the system to measure the parameters of the gas at those points, and the readings from these sensors can be used by a controller to estimate or calculate the characteristics of the gases at the point of delivery. The controller then adjusts the output parameters of the system (e.g. fan speed, power to the humidifier chamber heater plate, etc) accordingly. One example of a system and method where this type of calculation is carried out is disclosed in WO 2001/13981, which describes an apparatus where there are no sensors at the patient end of the conduit. A, temperature sensor is located proximal to the heater plate in order to measure the heater plate temperature. The flow of gases through the humidifier chamber is estimated, and the appropriate power level for the heater plate is then determined by a central controller. The controller estimates the power supply to the heater humidifier plate, and the power required by the conduit heater wire for achieving optimal temperature and humidity of the gases delivered to a patient.

One possible disadvantage of systems and methods which estimate the gases characteristics (such as the system and method disclosed in WO 2001/13981) is that the estimations and algorithms used are not as accurate as is necessary. There are many variable factors that can detrimentally effect the accuracy of the calculation algorithms used by the controller. These factors may not have been taken into consideration when the algorithm was designed. For example, the apparatus and in particular the humidifier chamber can be subject to convective heat loss ('draft') which is created by external airflows, particularly in ventilated spaces. The flow velocities of the air vary in magnitude, direction and fluctuation frequency. Mean air velocities from below 0.05 m/s up to 0.6 m/s, turbulence intensities from less than 10% up to 70%, and frequency of velocity fluctuations as high as 2 Hz that contribute up to 90% of the measured standard deviations of fluctuating velocity have been identified in the occupied zone of rooms—for one example, see Volume 13, number 6 of HVAC&R Research—paper titled: 'accuracy limitations for low velocity measurements and draft assessment in rooms', by A Melikov, Z Popiolek, and M. C. G. Silva.

The system disclosed in WO 2001/13981 is unlikely to be able to provide the control precision necessary to control humidity accurately without substantial rainout occurring. A user or manufacturer may be forced to trade-off delivery of gases at a lower humidity level, against an increased possibility of rain-out, against the number of sensors used and their location in the breathing circuit. For example, when the incoming gas delivered to the humidifier chamber from the compressor or blower (particularly in an integrated blower/humidifier breathing assistance system) has an increased temperature, the chamber temperature should be accurately compensated to achieve the desired dew point. If the air coming into the chamber is warm and the air temperature is increasing with an increase in flow, then the inaccuracy of a set calculation algorithm will increase.

It should further be noted that prior art systems frequently measure/calculate and display the humidifier chamber outlet temperature. Displaying the temperature reading is often inadequate for a user to make an informed decision, as the temperature does not always directly relate to the gases humidity state. This is due to a number of factors, of which the following are examples, but not an exhaustive list.

1. High temperature of the incoming gas.
2. Very low or very high flow rate.
3. Cooling of the humidifier chamber by convection of the ambient air around the humidification chamber.
4. Mixing of outgoing and incoming gases inside the chamber.
5. Condensation of water at the chamber wall or connection tubes particularly at low ambient temperature conditions.
6. Problems with accurate temperature measurements at high humidity (the 'wet bulb' effect).
7. Variations in the level of the humidity of the incoming gas.

Furthermore, a user may not always require gases warmed to body temperature and 100% humidity. A specific therapy regime may call for a high or 100% humidity level, but this can be undesirable for users who use a mask, as the conditioned gas with high humidity can feel uncomfortable for a user on their skin.

A further problem in system of this type can be outlined as follows: It is normal in systems such as those outlined above for the fan speed (modular and integrated units) or pressure/flow level (hospital, remote source units) to be set to a constant level, with the assumption that this will provide a constant flow rate throughout the system (or alternatively, if using a central gases source in the system, the flow rate of the incoming gases from the remote source is assumed to remain constant). A constant flow rate is desirable for the same or similar reasons as outlined above. A constant flow rate is also very desirable when using additional or supplementary oxygen, blending this with atmospheric gases. A constant flow rate will help to keep the oxygen fraction at the desired level.

As the gases characteristics are interdependent, a change in the flow rate may lead to a significant change in the humidity, temperature or oxygen fraction of the gases delivered to a user. However, the flow through the system may be affected by a number of different interdependent variables which are independent of the gases source (e.g. the speed of the fan). These can include increased (or decreased) resistance to flow caused by changes in the position of the user interface on a user, changes in the way the delivery conduit is bent in use, etc. The flow rate will also change if, for example, the interface is changed to a different size or shape of interface, or a different type of interface altogether.

There is therefore a need for a system and method which provides increased control precision for controlling the humidity, or temperature, or both, of the gases flow, while at the same time delivering gases to a patient at the correct temperature, humidity and pressure for effective therapy. There is also the need for a system which compensates for changes in the resistance to flow through the system during use in order to provide a substantially constant flow rate at the desired level.

SUMMARY OF THE INVENTION

It is an object of the present invention to provide an integrated blower/humidifier system that goes some way towards overcoming the above disadvantages, or which provides users with a useful choice.

In a first aspect the invention may broadly be said to consist in a breathing assistance system for delivering a stream of heated, humidified gases to a user for therapeutic purposes, comprising;

a humidifier unit that has an inlet port and an exit port, said humidifier unit adapted to in use receive a flow of gases from a gases source via said inlet port, said humidifier unit further adapted to hold and heat a volume of water in use, in use said flow of gases passing through said humidifier unit and becoming heated and humidified, said heated humidified gases exiting said humidifier unit via said humidifier unit exit port, an exit port temperature sensor adapted to measure the temperature of gases exiting said humidifier unit, an ambient temperature sensor adapted to measure the temperature of gases at a point before said gases enter said humidifier unit, a flow sensor adapted to measure the actual flow rate of said gases stream through said system, a controller adapted to receive data from said ambient temperature sensor relating to the measured temperature, data from said exit port temperature sensor relating to the measured temperature, and data from said flow sensor relating to said actual flow rate, said controller determining a control output in response, said control output adjusting the power to said humidifier unit to achieve a desired output at said humidifier unit exit port.

In a second aspect the invention may broadly be said to consist in a breathing assistance system for delivering a stream of heated, humidified gases to a user for therapeutic purposes, comprising;

a humidifier unit that has an inlet port and an exit port, said humidifier unit adapted to in use receive a flow of gases from a gases source via said inlet port, said humidifier unit further adapted to hold and heat a volume of water in use, in use said flow of gases passing through said humidifier unit and becoming heated and humidified, said heated humidified gases exiting said humidifier unit via said humidifier unit exit port, a delivery conduit and user interface configured to in use receive said heated humidified gases from said exit port for delivery to said user, said delivery conduit having a heater wire adapted to heat the gases within said conduit, a patient end temperature sensor adapted to measure the temperature of said gases flow at or close to said patient, a flow probe adapted to measure the actual flow rate of said gases stream through said system, said breathing assistance system further comprising a controller adapted to receive data from said patient end temperature sensor relating to the measured temperature, and data from said flow probe relating to said actual flow rate, said controller determining a control output in response, said control output adjusting the power to at least said heater wire to maintain or alter the temperature of said flow of gases within said conduit to achieve a desired patient end temperature and absolute humidity at said interface.

Preferably said control output relates to a target temperature at said exit port for a given flow level, and said desired output is a target temperature, said control output adjusting said power to said humidifier unit to match said measured temperature at said exit port with said target temperature.

Preferably said control output is determined from a rule-based system loaded in said controller.

Alternatively said control output is determined from at least one mathematical formula loaded in said controller.

Alternatively said control output is determined from a look-up table loaded in said controller.

Preferably said desired output is a target dew point temperature.

Preferably said target dew point temperature is in the range 31-39° C.

Preferably said user set target dew point temperature provides an absolute humidity level of substantially 44 mg $H_2O$/liter of air.

Alternatively said desired output is a target absolute humidity.

Alternatively said desired output is a target temperature and relative humidity.

Preferably said breathing assistance system also has user controls adapted to enable a user to set a desired user-set flow rate of gases through said system.

Preferably said breathing assistance apparatus further comprises a control unit adapted to in use receive a flow of gases from a remote central source, said control unit located in the gases path between said central source and said humidifier unit, said control unit receiving said flow of gases and passing said flow on to said humidifier unit via a gases connection path between said humidifier unit and said control unit, said user controls adapted to enable a user to set a desired user-set flow rate through said control unit.

Preferably said control unit further comprises a venturi adapted to mix said flow of gases from said central source with atmospheric gases before passing these to said humidifier unit.

Preferably said gases source is a blower unit fluidically connected in use to said humidifier unit, said blower unit having an adjustable, variable speed fan unit adapted to deliver said flow of gases over a range of flow rates to said humidifier unit and user controls adapted to enable a user to set a desired user-set flow rate, said controller adapted to control the power to said blower unit to produce said user-set flow rate.

Preferably said humidifier unit is a humidifier chamber having a heater base, and said breathing assistance system further has a heater plate adapted to heat the contents of said humidifier chamber by providing heat energy to said heater base, said breathing assistance system further having a heater plate temperature sensor adapted to measure the temperature of said heater plate and provide this temperature measurement to said controller, said controller determining said control output by assessing all of said measured temperatures and said measured flow rate.

Preferably if a target value of said chamber gases outlet temperature is reached and the corresponding heater plate temperature is higher than a set value stored in the memory of said controller for a given pre-set time period, said controller assesses that said humidifier unit is experiencing high convective heat loss and determines said control output according to an altered or different rule set, mathematical formula or look-up table.

Preferably said controller is further adapted to measure the power drawn by said heater plate for a given pre-set time period and if the power drawn is higher than a value stored in the memory of said controller, said controller assesses that said humidifier unit is experiencing high convective heat loss and determines said control output according to an altered or different control algorithm, mathematical formula or look-up table.

Preferably said controller is further adapted to measure the power drawn by said heater plate for a given pre-set time period and compare this to a pre-stored set of values stored in the memory of said controller, said controller applying an inversely linear correction factor if the measured power drawn is not substantially similar to said pre-stored set of values.

Preferably said measured data values and said stored data values must be within +/−2%.

Preferably said ambient temperature sensor is located at or close to said inlet port to measure the temperature of gases substantially as they enter said humidifier unit.

Alternatively said ambient temperature sensor is adapted to measure the pre-entry temperature of gases substantially as they enter said breathing assistance system, said controller applying a correction factor to said pre-entry temperature.

Preferably said controller is adapted to receive at least said user set flow rate and said actual flow rate data from said flow probe or flow sensor, said controller having a coarse control parameters and fine control parameters, said controller comparing said user set flow rate and said actual flow rate, said controller using said fine control parameters to adjust the output of said fan to match said actual flow rate to said user set flow rate as long as said actual flow rate matches said user set flow rate to within a tolerance, the value of said tolerance stored within said controller, said controller using said coarse control parameters to adjust the output of said fan to match said actual flow rate to said user set flow rate if the difference between said user set flow rate and said actual flow rate is outside said tolerance.

Preferably said coarse control parameters are a first P.I.D. filter and said fine control parameters are a second P.I.D. filter.

Alternatively said controller further comprises a compensation filter, a low pass filter, a high pass filter, and a P.I.D. filter, said signal indicative of actual flow rate from said flow probe passed in parallel through said low pass filter and said high pass filter, said low pass filter producing a low pass output signal, said high pass filter producing a high pass output signal that is passed through said compensation filter, said low pass output signal subtracted from said user set flow rate signal and passed into said P.I.D filter, the output signal from said P.I.D filter and the output signal from said compensation filter summed and compared to said user set flow rate, said controller using said coarse control parameters to adjust the output of said fan to match said actual flow rate to said user set flow rate if the difference between the sum of said output signals and the user set flow rate is outside a pre-set tolerance contained in the memory of said controller.

Alternatively said controller is adapted to receive at least said user set flow rate and said actual flow rate data from said flow probe, said controller having a coarse control parameters and fine control parameters, said controller comparing said user set flow rate and said actual flow rate, said controller using said fine control parameters to adjust the output of said fan to match said actual flow rate to said user set flow rate as long as said actual flow rate matches said user set flow rate to within a tolerance, the value of said tolerance stored within said controller, said controller using said coarse control parameters to adjust the output of said fan to match said actual flow rate to said user set flow rate if the difference between said user set flow rate and said actual flow rate is outside said tolerance.

Alternatively said controller further comprises a compensation filter, a low pass filter, a high pass filter, and a P.I.D. filter, said signal indicative of actual flow rate from said flow probe passed in parallel through said low pass filter and said high pass filter, said low pass filter producing a low pass output signal, said high pass filter producing a high pass output signal that is passed through said compensation filter, said low pass output signal subtracted from said user set flow rate signal and passed into said P.I.D filter, the output signal from said P.I.D filter and the output signal from said compensation filter summed and compared to said user set flow rate, said controller using said coarse control parameters to adjust the output of said fan to match said actual flow rate to said user set flow rate if the difference between the sum of said output signals and the user set flow rate is outside a pre-set tolerance contained in the memory of said controller.

Preferably said controller also includes a feedback signal from said fan to said compensation filter so that the input signal to said fan unit comprises the output signal from said P.I.D. filter and the output signal from said compensation filter.

Preferably said actual flow rate data is measured by said at least one flow probe, said actual flow rate data subtracted from said user set flow data and a signal indicative of the difference sent to both said first and second P.I.D. filters, said controller using either the output of said first P.I.D. filter or said second P.I.D. filter to adjust the output of said fan to match said actual flow rate to said user set flow rate.

Preferably said flow rate is sampled at a sample rate of between 20 and 30 Hz.

Even more preferably said sample rate is 25 Hz.

Preferably said actual flow rate data is passed through a first low-pass filter before being subtracted from said user set flow data.

Preferably said first low-pass filter has a cut-off frequency high enough to allow intra breath flow variation to pass unattenuated.

Preferably said actual flow rate data is also passed through an averaging filter.

Preferably said averaging filter is a second low pass filter.

Preferably the output of said averaging filter is fed back to said controller in place of said direct flow data from said flow probe.

Preferably said controller receives said averaged flow from said averaging filter and compares this to said user set flow rate, said controller using coarse control parameters to adjust the flow rate to said user set rate if the difference between said user set flow rate and said actual flow rate is outside a tolerance value stored in the memory of said controller, said controller using fine control parameters if said difference is inside said tolerance.

Preferably said tolerance is 3 L/min.

Alternatively said tolerance is variable, and is a percentage value of said actual flow rate as measured by said flow probe.

Preferably said percentage value is between 1-3%.

Alternatively said percentage value is between 3-5%.

Alternatively said percentage value is between 5-7%.

Alternatively said percentage value is between 7-10%.

Preferably said control unit is particularly adapted to receive oxygen as said gases from said remote source, said at least one flow probe adapted to measure said flow rate of gases received from said remote source and pass said flow rate measurement on to said controller, said controller adapted to determine the flow rate of said gases from atmosphere based on the known system dimensions, said controller determining the fraction of oxygen in said blended air from said flow rate and said system dimensions.

Preferably said control unit is adapted to receive oxygen as said gases from said remote source, said at least one flow probe adapted to measure said flow rate of gases received from said remote source, said system further comprising a second flow probe adapted to measure the flow rate of said gases received from atmosphere, said controller determining the fraction of oxygen in said blended air from said flow rates.

Preferably said system is adapted so that when a user alters said user set flow rate this alters said oxygen fraction.

Preferably said system further has a display adapted to show chamber outlet dew point temperature.

Alternatively said display is adapted to show the absolute humidity level of gases exiting said chamber.

Alternatively said display is adapted to show absolute humidity and chamber outlet dew point temperature.

Preferably said breathing assistance system also has a humidity sensor adapted to measure the humidity of atmospheric gases entering said breathing assistance system, said controller receiving data relating to the measured humidity, said controller determining said control output by also using said data relating to the measured humidity.

Preferably said system also has a pressure sensor adapted to measure the pressure of atmospheric gases entering said breathing assistance system, said controller receiving data relating to the measured pressure, said controller determining said control output by also using said data relating to the measured pressure.

Preferably said system further comprises a delivery conduit and user interface configured to in use receive said heated humidified gases from said exit port for delivery to said user, said delivery conduit having a heater wire adapted to heat the gases within said conduit.

Preferably said breathing assistance system further has a patient end temperature sensor adapted to measure the temperature of said gases flow at or close to said patient, the measured patient end temperature fed back to said controller, said controller adjusting the power to said heater wire to maintain the temperature of said flow of gases within said conduit.

Preferably said controller receives said measured patient end temperature data, said controller determining said control output by also using said data relating to the measured patient end temperature data.

Preferably said controller is further adapted to measure the power drawn by said heater wire for a given pre-set time period, and if said power drawn by said heater wire is higher than a value stored in the memory of said controller, said controller assesses that said humidifier unit is experiencing high convective heat loss and determines said control output according to an altered or different rule set, mathematical formula, or look-up table.

This invention may also be said broadly to consist in the parts, elements and features referred to or indicated in the specification of the application, individually or collectively, and any or all combinations of any two or mote of said parts, elements or features, and where specific integers are mentioned herein which have known equivalents in the art to which this invention relates, such known equivalents are deemed to be incorporated herein as if individually set forth.

The term 'comprising' as used in this specification means 'consisting at least in part of', that is to say when interpreting statements in this specification which include that term, the features, prefaced by that term in each statement, all need to be present but other features can also be present.

BRIEF DESCRIPTION OF THE DRAWINGS

One preferred form of the present invention will now be described with reference to the accompanying drawings in which.

DETAILED DESCRIPTION OF THE PREFERRED EMBODIMENTS

Figure 2A:
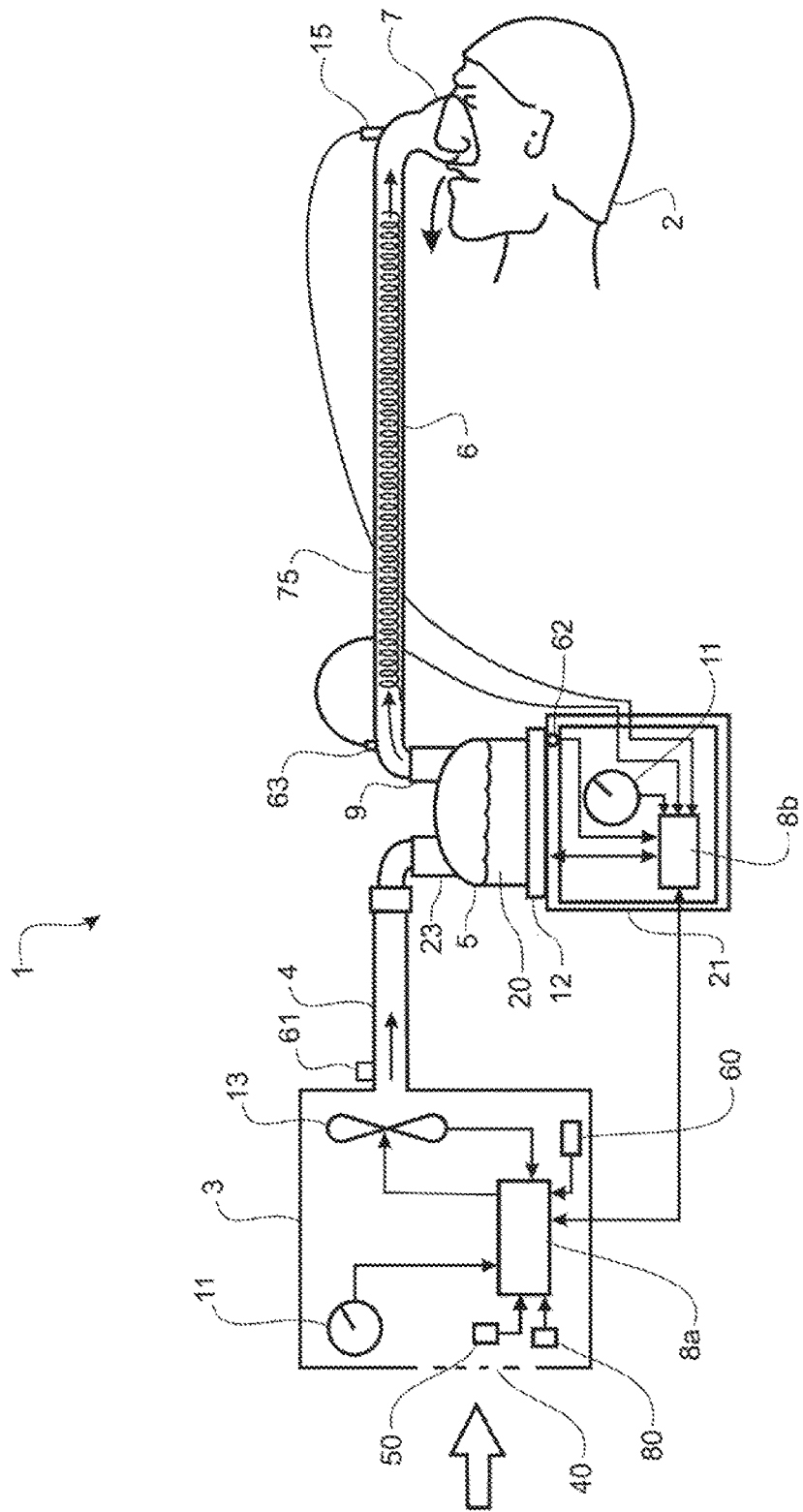
FIG. 2a shows a schematic view of a user receiving humidified air from one variant of the present invention, with the user wearing a nasal mask and receiving air from a modular blower/humidifier breathing assistance system.
Figure 2B:
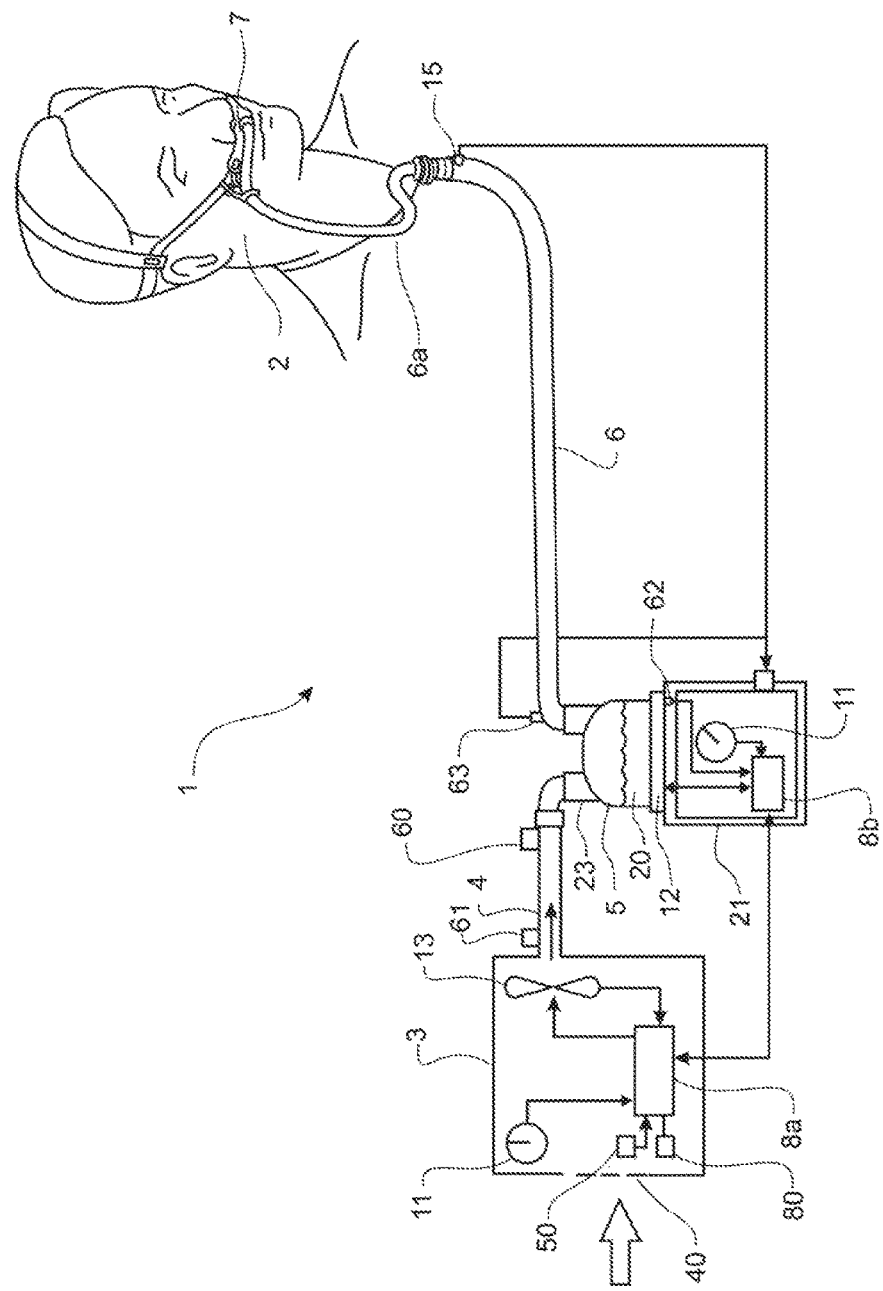
FIG. 2b shows a schematic view of a user receiving humidified air from another variant of the present invention, where the user is wearing a nasal cannula and receiving air from a modular blower/humidifier breathing assistance system.

A schematic view of a user 2 receiving air from a modular assisted breathing unit and humidifier system 1 according to a first variant or embodiment of the invention is shown in FIGS. 2a and 2b. The system 1 provides a pressurised stream of heated, humidified gases to the user 2 for therapeutic purposes (e.g. to reduce the incidence of obstructive sleep apnea, to provide CPAP therapy, to provide humidification for therapeutic purposes, or similar) The system 1 is described in detail below.

Figure 7:
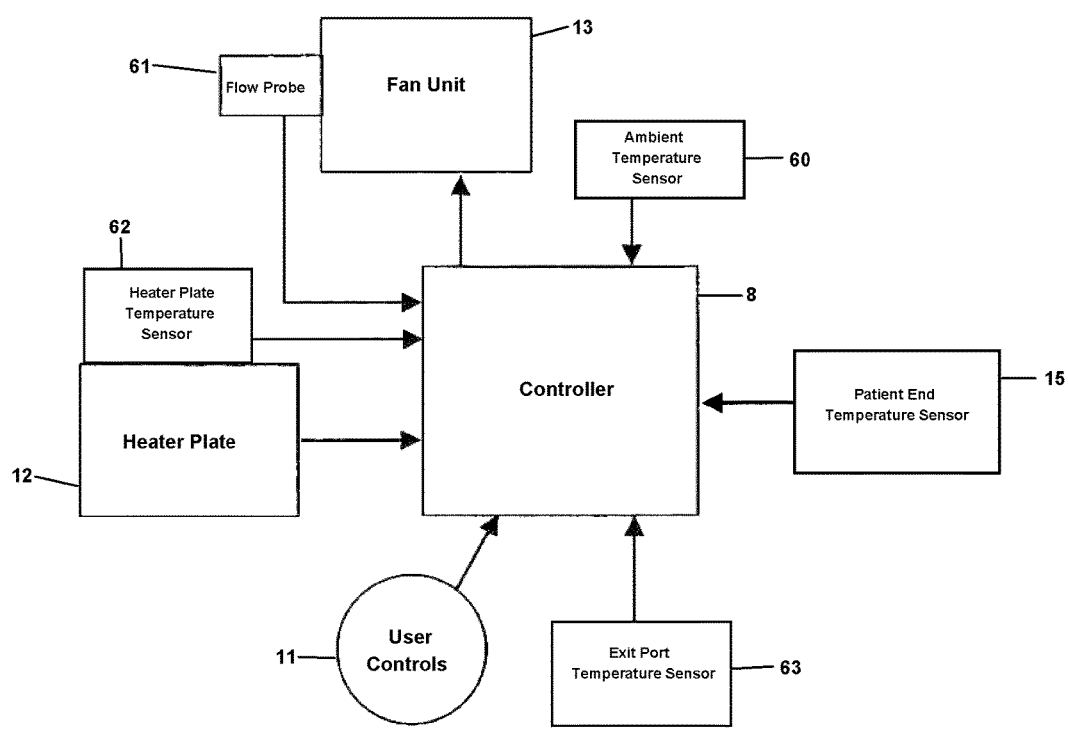
FIG. 7 shows a schematic representation of some of the connections between a controller suitable for use with the breathing assistance system of FIG. 2, 3 or 4, and other components of the preferred form of breathing assistance system as shown in FIG. 2, 3, or 4.

The assisted breathing unit or blower unit 3 has an internal compressor unit, flow generator or fan unit 13—generally this could be referred to as a flow control mechanism. Air from atmosphere enters the housing of the blower unit 3 via an atmospheric inlet 40, and is drawn through the fan unit 13. The output of the fan unit 13 is adjustable—the fan speed is variable. The pressurised gases stream exits the fan unit 13 and the blower unit 3 and travels via a connection conduit 4 to a humidifier chamber 5, entering the humidifier chamber 5 via an entry port or inlet port 23. The humidifier chamber 5 in use contains a volume of water 20. In the preferred embodiment, in use the humidifier chamber 5 is located on top of a humidifier base unit 21 which has a heater plate 12. The heater plate 12 is powered to heat the base of the chamber 5 and thus heat the contents of the chamber 5. As the water in the chamber 5 is heated it evaporates, and the gases within the humidifier chamber 5 (above the surface of the water 20) become heated and humidified. The gases stream entering the humidifier chamber 5 via inlet port 23 passes over the heated water (or through these heated, humidified gases—applicable for large chamber and flow rates) and becomes heated and humidified as it does so. The gases stream then exits the humidifier chamber 5 via an exit port or outlet port 9 and enters a delivery conduit 6. When a 'humidifier unit' is referred to in this specification with reference to the invention, this should be taken to mean at least the chamber 5, and if appropriate, the base unit 21 and heater plate 12. The heated, humidified gases pass along the length of the delivery conduit 6 and are provided to the patient or user 2 via a user interface 7. The conduit 6 may be heated via a heater wire (not shown) or similar to help prevent rain-out. The user interface 7 shown in FIG. 2a is a nasal mask which surrounds and covers the nose of the user 2. However, it should be noted that a nasal cannula (as shown in FIG. 2b), full face mask, tracheostomy fitting, or any other suitable user interface could be substituted for the nasal mask shown. A central controller or control system 8 is located in either the blower casing (controller 8a) or the humidifier base unit (controller 8b). In modular systems of this type, it is preferred that a separate blower controller 8a and humidifier controller 8b are used, and it is most preferred that the controllers 8a, 8b are connected (e.g. by cables or similar) so they can communicate with one another in use. The control system 8 receives user input signals via user controls 11 located on either the humidifier base unit 21, or on the blower unit 3, or both. In the preferred embodiments the controller 8 also receives input from sensors located at various points throughout the system 1. FIG. 7 shows a schematic representation of some of the inputs and outputs to and from the controller 8. It should be noted that not all the possible connections and inputs and outputs are shown—FIG. 7 is representative of some of the connections and is a representative example. The sensors and their locations will be described in more detail below. In response to the user input from controls 11, and the signals received from the sensors, the control system 8 determines a control output which in the preferred embodiment sends signals to adjust the power to the humidifier chamber heater plate 12 and the speed of the fan 13. The programming which determines how the controller determines the control output will be described in more detail below.

Figure 3:
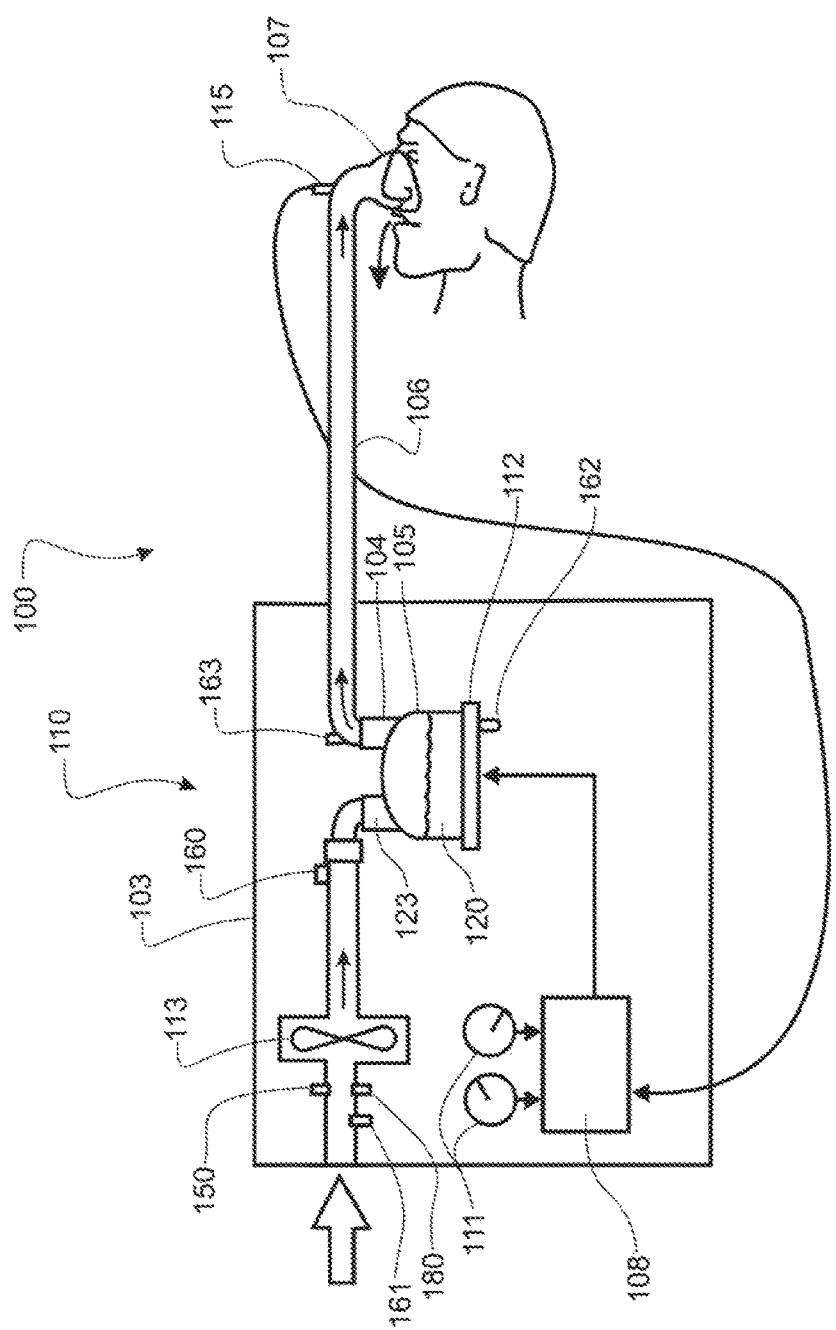
FIG. 3 shows a schematic view of a user receiving humidified air from another variant of the present invention, where the user is wearing a nasal mask and receiving air from an integrated blower/humidifier breathing assistance system.

A schematic view of the user 2 receiving air from an integrated blower/humidifier system 100 according to a second form of the invention is shown in FIG. 3. The system operates in a very similar manner to the modular system 1 shown in FIG. 2 and described above, except that the humidifier chamber 105 has been integrated with the blower unit 103 to form an integrated unit 110. A pressurised gases stream is provided by fan unit 113 located inside the casing of the integrated unit 110. The water 120 in the humidifier chamber 105 is heated by heater plate 112 (which is an integral part of the structure of the blower unit 103 in this embodiment). Air enters the humidifier chamber 105 via an entry port 123, and exits the humidifier chamber 105 via exit port 109. The gases stream is provided to the user 2 via a delivery conduit 106 and an interface 107. The controller 108 is contained within the outer shell of the integrated unit 100. User controls 111 are located on the outer surface of the unit 100.

Figure 4:
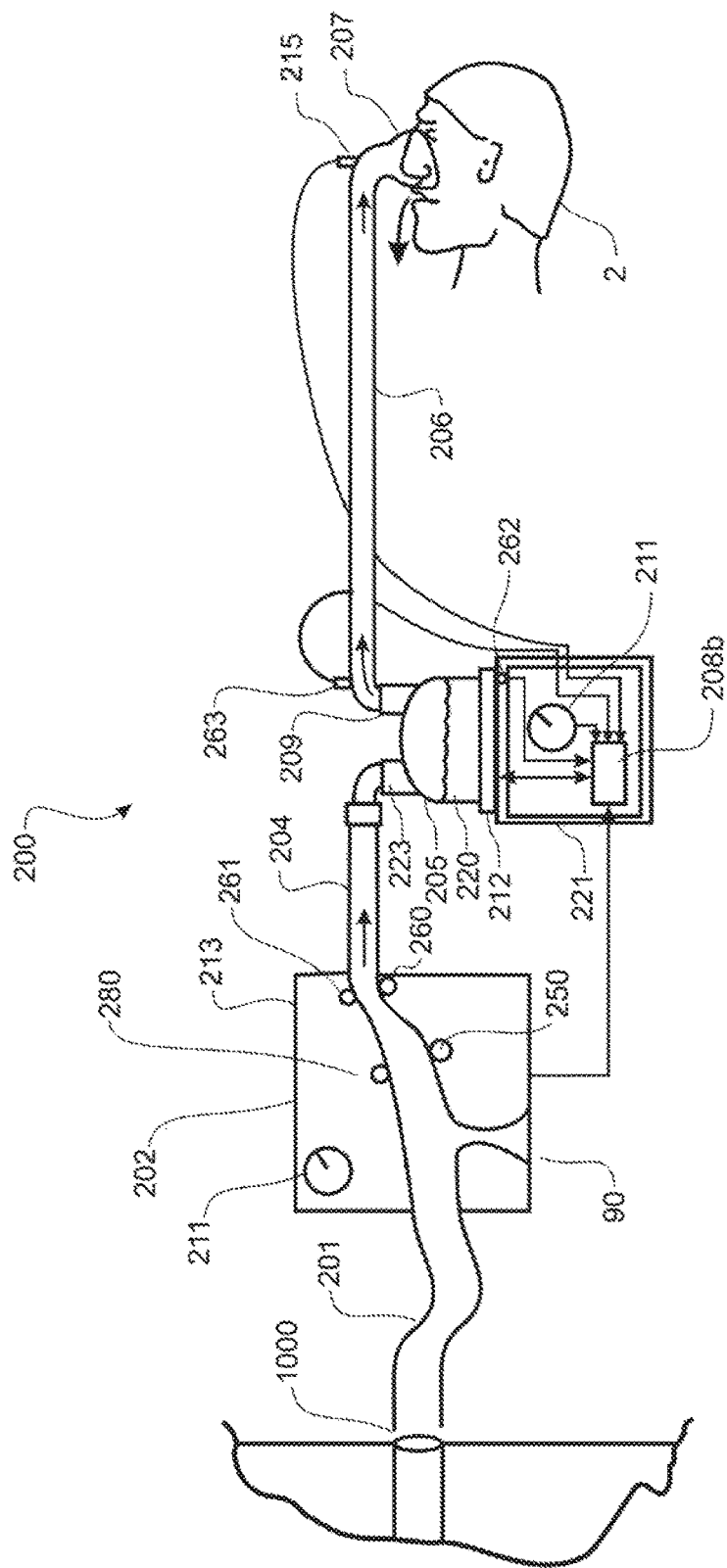
FIG. 4 shows a schematic view of a user receiving humidified air from another variant of the present invention, where the user is wearing a nasal cannula, the breathing assistance system receiving gases from a central source via a wall inlet and providing these to a control unit, which provides the gases to a humidifier chamber in line with and downstream of the control unit.

A schematic view of the user 2 receiving air from a further form of breathing assistance system 200 is shown in FIG. 4. The system 200 can be generally characterised as a remote source system, and receives air from a remote source via a wall inlet 1000. The wall inlet 1000 is connected via an inlet conduit 201 to a control unit 202, which receives the gases from the inlet 1000. The control unit 202 has sensors 250, 260, 280, 290 which measure the humidity, temperature and pressure and flow respectively of the incoming gases stream. The gases flow is then provided to a humidifier chamber 205, with the gases stream heated and humidified and provided to a user in a similar manner to that outlined above. It should be noted that when 'humidifier unit' is referred to for a remote source system such as the system 200, this should be taken to mean as incorporating the control unit 202—the gases from the remote source can either be connected directly to an inlet, or via the control unit 202 (in order to reduce pressure or similar), but the control unit and the humidifier chamber should be interpreted as belonging to an overall 'humidifier unit'. If required, the system 200 can provide $O_2$ or an $O_2$ fraction to the user, by having the central source as an $O_2$ source, or by blending atmospheric air with incoming $O_2$ from the central source via a venturi 90 or similar located in the control unit 202. It is preferred that the control unit 202 also has a valve or a similar mechanism to act as a flow control mechanism to adjust the flow rate of gases through the system 200.

Sensors

The modular and integrated systems 1, 100 and 200 shown in FIGS. 2, 3 and 4 have sensors located at points throughout the system. These will be described below in relation to the breathing assistance system 1.

The preferred form of modular system 1 as shown in FIG. 2 has at least the following sensors in the following preferred locations:

1) An ambient temperature sensor 60 located within, near, or on the blower casing, configured or adapted to measure the temperature of the incoming air from atmosphere. It is most preferred that temperature sensor 60 is located in the gases stream after (downstream of) the fan unit 13, and as close to the inlet or entry to the humidifier chamber as possible.

2) A humidifier unit. exit port temperature sensor 63 located either at the chamber exit port 9, or located at the apparatus end (opposite to the patient end) of the delivery conduit 6. Outlet temperature sensor 63 is configured or adapted to measure the temperature of the gases stream as it exits chamber 5 (in either configuration the exit port temperature sensor 63 can be considered to be proximal to the chamber exit port 9).

Similarly, sensors are arranged in substantially the same locations in the integrated system 100 shown in FIG. 3 and the system 200 of FIG. 4. For example, for the integrated system of FIG. 3, an ambient temperature sensor 160 is located within the blower casing in the gases stream, just before (upstream of) the humidifier chamber entry port 123. A chamber exit port temperature sensor 163 is located either at the chamber exit port 109 and is configured to measure the temperature of the gases stream as it exits chamber 105 (in either configuration the exit port temperature sensor 163 can be considered to be proximal to the chamber exit port 109). Alternatively, this sensor can be located at the apparatus end (opposite to the patient end) of the delivery conduit 106, for either embodiment. A similar numbering system is used for the breathing assistance system shown in FIG. 4—ambient temperature sensor 260, fan unit 213, chamber exit port temperature sensor 263 located at the chamber exit port 209, etc.

It is also preferred that the breathing assistance system 1 (and 100, 200) also has a heater plate temperature sensor 62 located adjacent to the heater plate 12, configured to measure the temperature of the heater plate. The breathing assistance system(s) having a heater plate temperature sensor is preferred as it gives an immediate indication of the state of the heater plate. However, it is not absolutely necessary to for the system(s) to have the heater plate temperature sensor in order to reduce the invention to practice.

It is also most preferred that the systems also have a flow probe—flow probe 61 in system 1—located upstream of the fan unit 13 and configured to measure the gases flow. The preferred location for the flow probe is upstream of the fan unit, although the flow probe can be located downstream of the fan, or anywhere else appropriate. Again, it is preferred that a flow probe forms part of the system, but it is not absolutely necessary for a flow probe to be part of the system to reduce the invention to practice.

The layout and operation of the breathing assistance system 1 will now be described below in detail. The operation and layout of the systems 100 and 200 is substantially the same, and will not be described in detail except where necessary.

For the breathing assistance system 1, the readings from all of the sensors are fed back to the control system 8. The control system 8 also receives input from the user controls 11.

Further alternative additional sensors and their layout will be described in more detail later.

Humidity Control Method

In the most preferred embodiment, the control system 8 has at least one data set pre-loaded into the controller. The data that forms the data set is pre-measured or pre-calculated under controlled conditions (e.g. in a test area or laboratory) for a specific system configuration with specific components (e.g. system 1 or system 100, or system 200, with a particular, specific blower unit and humidifier unit used to gather the data). The data is gathered under a number of condition ranges that will typically be encountered in use, with the pre-measured (pre-set) data then being loaded as integral software or hardware into the controller 8 for the production systems, or as data to be used in e.g. a fuzzy logic algorithm for humidity control.

Figure 5:
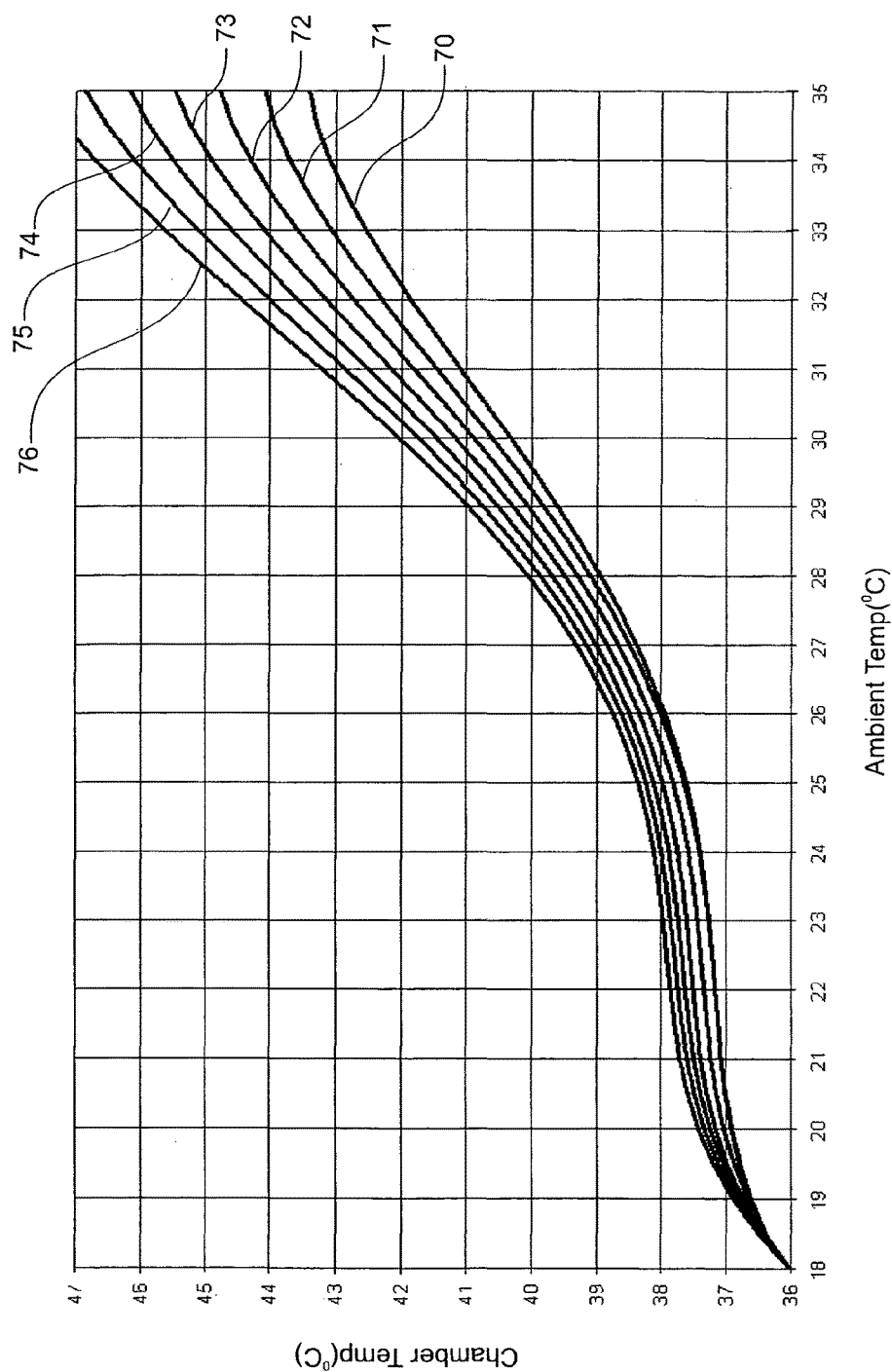
FIG. 5 shows a graphical representation of a data set for use with the breathing assistance system of FIG. 2 or 3, the graph showing curves representative of seven different constant flow rates over a range of ambient atmospheric temperatures, and a range of target temperatures for a given flow and ambient temperature, the data loaded into the system controller in use.

A data set particularly suitable for use with system 1 is shown as a graph in FIG. 5. The X-axis shows a range of ambient temperatures, from 18° C. to 35° C. In use, the ambient temperature of the gases in the breathing assistance system before or upstream of the chamber 5 is measured by the ambient temperature sensor 60, and the ambient temperature data is relayed to the controller 8. It is most preferred that the temperature sensor 60 measures the ambient temperature of the gases just before the gases enter the chamber 5. In order to create the data set, a typical system 1 is placed in an environment where the ambient temperature can be kept at a known, constant level over a range of temperatures.

In the preferred form in use, a user chooses a flow rate by adjusting the controls 11. The controller 8 receives the input from the user controls 11 and adjusts the fan speed to substantially match this requested flow rate (either by altering the speed of the fan to a speed that is known to substantially correspond to the required flow for the particular breathing circuit configuration, or by measuring the flow using flow probe 61 and using a feedback mechanism via controller 8 to adjust the flow rate to the level required or requested). Seven different constant flow rates are shown in the graph of FIG. 5, for seven different constant fan speeds. The lines 70-76 correspond to different flow rates as follows: Line 70—a flow rate 15 liters/minute. Line 71—a flow rate of 20 liters/minute. Line 72—a flow rate of 25 liters/minute. Line 73—a flow rate of 30 liters/minute. Line 74—a flow rate of 35 liters/minute. Line 75—a flow rate of 40 liters/minute. Line 76—a flow rate of 45 liters/minute.

The Y-axis shows a range of target chamber temperatures. That is, for any given fan speed (flow rate and pressure), and any given ambient temperature, there is a 'best', or 'ideal' target outlet temperature for the gases in the chamber 5 above the water 20—the target outlet temperature as shown on the Y-axis. This 'ideal' temperature is the dew point temperature for a given constant flow and constant ambient temperature. That is, the temperature at which the gases can exit the chamber 5 at the required saturation (required level of humidity) and then be delivered to the user 2 at the correct temperature and pressure for effective therapy. As the gases exit the chamber 5, the gases temperature is measured by the chamber exit port temperature sensor 63. The controller 8 is adapted to receive the temperature data measured by the chamber exit temperature sensor 63 and the data relating to the temperature of the gases entering the chamber 5 (as measured by ambient temperature sensor 60). The flow rate has been previously set to a constant value, as outlined above, so the controller 8 already 'knows' the constant flow rate. As the controller 8 'knows' both the flow rate and the ambient temperature, it can, for example, look up the 'ideal' target outlet temperature from the range incorporated into the pre-loaded data set (e.g. the data shown graphically in FIG. 5). The controller 8 then compares the measured value of chamber exit temperature to the 'ideal' target chamber temperature for the given, known flow rate and ambient temperature. If the measured value of target temperature does not match the 'ideal' target value, the controller 8 generates or determines a suitable control output, and adjusts the power to the heater plate accordingly, either increasing the power to increase the temperature of the gases within the chamber 5, or decreasing the power to decrease the gases temperature. The controller 8 adjusts the power in this manner in order to match the temperature measured at the outlet or exit port with the required target temperature. In the preferred embodiment, the mechanism by which the controller 8 adjusts the output characteristics is via a Proportional—Integral—Derivative controller (P.I.D. controller) or any one of a number of similar mechanisms which are known in the art.

The controller could also generate or determine a suitable control output by, for example, using a fuzzy logic control algorithm loaded into the controller 8, or mathematical formulae which utilise the measured temperature and flow data as variables in the equations.

Examples of mathematical formulae are shown below. These correspond generally to the data shown graphically in FIG. 5, for the range of flow rates from 15 to 45 liters/min.

| | |
|---|---|
| 45 | $T_{CS} = -0.0005 T_{amb}^4 + 0.055 T_{amb}^3 - 2.1234 T_{amb}^2 + 35.785 T_{amb} - 186.31$ |
| 40 | $T_{CS} = -0.0005 T_{amb}^4 + 0.0578 T_{amb}^3 - 2.2311 T_{amb}^2 + 37.554 T_{amb} - 196.98$ |
| 35 | $T_{CS} = -0.0006 T_{amb}^4 + 0.0625 T_{amb}^3 - 2.4283 T_{amb}^2 + 41.178 T_{amb} - 221.29$ |
| 30 | $T_{CS} = -0.0006 T_{amb}^4 + 0.0669 T_{amb}^3 - 2.6156 T_{amb}^2 + 44.613 T_{amb} - 244.25$ |
| 25 | $T_{CS} = -0.0006 T_{amb}^4 + 0.0696 T_{amb}^3 - 2.7315 T_{amb}^2 + 46.76 T_{amb} - 258.75$ |
| 20 | $T_{CS} = -0.0007 T_{amb}^4 + 0.0736 T_{amb}^3 - 2.8942 T_{amb}^2 + 49.651 T_{amb} - 277.53$ |
| 15 | $T_{CS} = -0.0007 T_{amb}^4 + 0.0776 T_{amb}^3 - 3.0612 T_{amb}^2 + 52.611 T_{amb} - 296.71$ |

Example

The therapy regime of a user 2 specifies a certain flow rate and pressure, for example a flow of 45 liters/min. The speed of the blower or fan unit 13 is set (via the controls 11) to deliver gases at this flow rate. If a flow probe 61 is part of the system, this flow rate can be dynamically adjusted by feeding back a real-time flow reading from the flow sensor or flow probe 61 to the controller 8, with the controller 8 adjusting the fan speed as necessary. This can be done via a P.I.D. controller that comprises part of the controls 8 as described in detail below, or similar. It is preferred that the flow rate is dynamically adjusted and monitored. However, if a flow probe is not part of the system, then the flow rate is assumed or calculated from the fan speed, and is assumed to be constant for a constant fan power level. The flow rate of 45 liters/minute is shown by line 76 on the graph of FIG. 5. In this example, the user 2 is sleeping in a bedroom having an ambient temperature of substantially 30° C. Air at 30° C. enters the breathing assistance apparatus and as it passes through the fan and connecting passages within the casing, it warms up slightly. The temperature of the air just before it enters the humidifier chamber is measured by the ambient temperature sensor 60. As the ambient temperature and the flow rate are known, the controller 8 can calculate the required target temperature, as shown on the Y-axis of the graph of FIG. 5. For this particular example, it can be seen that the chamber target temperature is 42° C. The chamber exit temperature sensor 63 measures the temperature of the gases as they exit the chamber 5 (the gases temperature at the exit point will be substantially the same temperature as the gases in the space above the chamber contents 20). If the gases temperature as measured by the chamber exit temperature sensor 63 is not 42° C., then the controller 8 determines and generates a suitable control output which alters the power to the heater plate 12 accordingly. As above, if the ambient temperature as measured by the ambient temperature sensor 60 changes, this can be fed back to the controller 8 and the outputs altered as appropriate using a P.I.D. control algorithm or similar.

One of the advantages of this system over the systems disclosed in the prior art is as follows: in prior art systems, as the ambient temperatures approach the target dew point temperature, the heater plate will draw less power and not raise the temperature of the water in the humidifier chamber as much. Therefore the gases will tend not to be fully saturated as they exit the chamber. The method outlined above overcomes this problem by using values of ambient temperature or more preferably chamber inlet temperature, chamber exit temperature and flow rate for a system of a known configuration, in order to produce a target chamber exit temperature which is considered to be substantially the best or 'ideal' temperature for gases saturation and delivery to a user for a set flow rate and a particular ambient temperature.

Another advantage is that the system 1 can accurately control the humidity level without the need for an accurate humidity sensor.

Another advantage is that when gas is delivered to the humidifier chamber from the compressor or blower, and this incoming gas has an increased temperature, the chamber temperature can be accurately compensated to achieve the desired dew point. This is particularly advantageous if the air or gases entering the chamber are warm, and also in situations when the temperature increases as the flow increases. In operation, any flow generator causes an increase in air temperature between the inlet from atmosphere and the outlet. This change in temperature can be more pronounced in some types of flow generator. The temperature of components of the system can change between the time at which the system is first activated and some time afterwards (e.g. over a reasonably prolonged period of time such as 1-2 hours). That is, components of the system can heat up as the system is operating, with the system taking some time to reach a steady state of operation. If these components are located in or adjacent to the air path between the point at which air enters the system, and the point at which the air enters the chamber, then the temperature of these gases is going to change—there is going to be some heat transfer from these components to the gases as the gases travel along this path. It can therefore be seen that measuring the temperature of the gases as they enter the chamber reduces the likelihood of introducing a temperature measurement error into the control calculations, as the temperature of the gases at the point of entry to the system when the system has reaches a steady state of operation may be different from the temperature of the gases at the point of entry to the chamber. However, it has generally been found that although it is most preferable to measure gases temperature at the point of entry to the chamber, it is also acceptable in most circumstances to measure atmospheric gases temperature.

The method described above is substantially similar for the integrated apparatus 100, or the apparatus 200, although the pre-set or pre-measured and pre-loaded values in the look-up table may differ as the apparatus has a slightly different configuration. In other forms, the user could choose a pressure rate (and the data set would be modified for pressure values rather than flow values).

The apparatus and method described above has been found to provide improved control of the gases characteristics at the point of delivery to the user 2, over systems and methods known in the prior art. The system and method described above goes some way towards overcoming the problems with prior art methods and apparatus. The system and method described above controls the output characteristics with the aim of producing gases at the chamber exit which are fully saturated—that is, the gases exiting the chamber are at dew point or very close to dew point for a given temperature. The system output characteristics are varied for the target dew point temperature, rather than the chamber exit temperature.

Figure 8A:
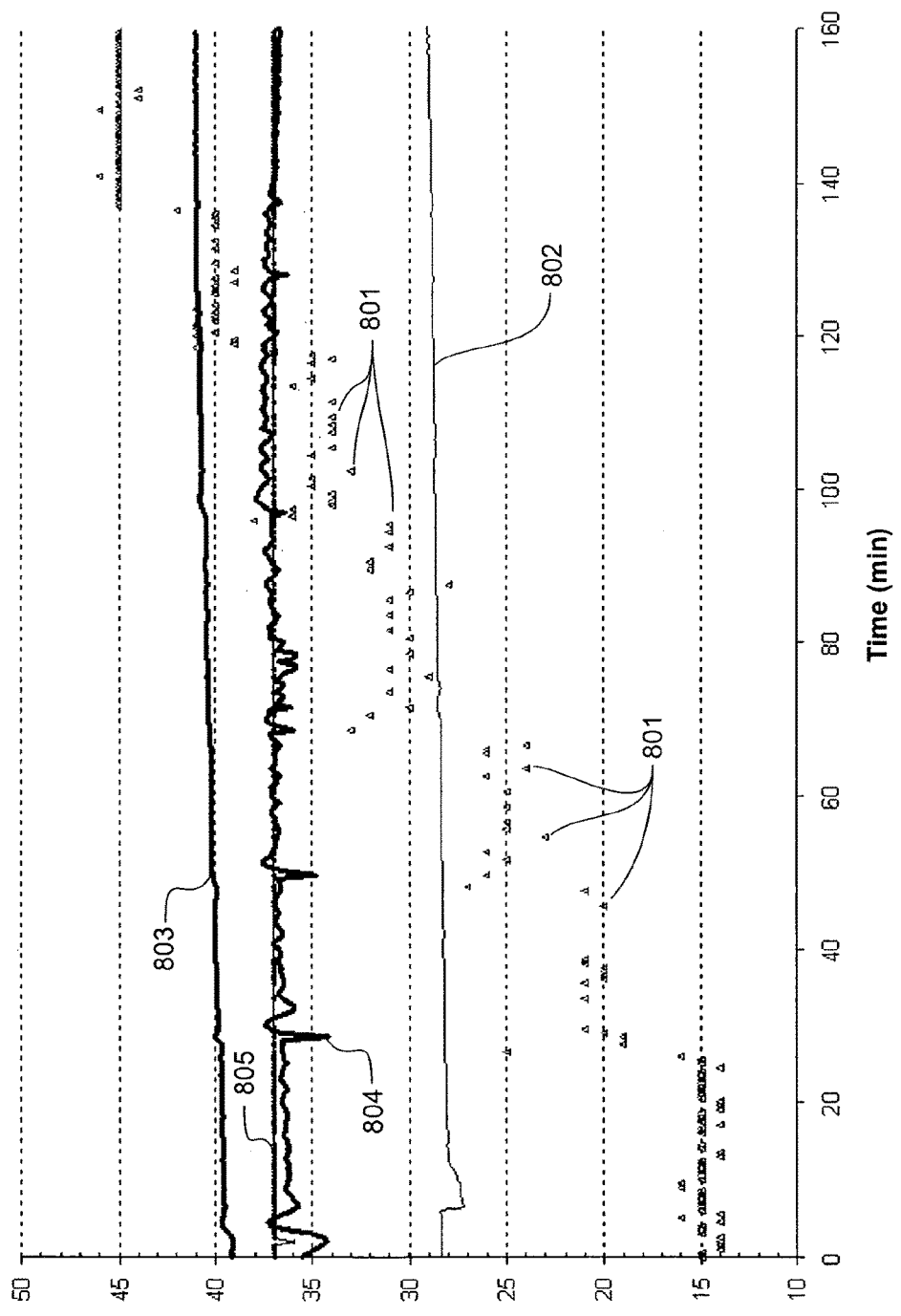
FIG. 8a shows a graph of measured experimental data of flow, dew point, chamber exit or chamber outlet temperature under conditions of high ambient temperature using a breathing assistance system such as that shown in FIG. 2, 3 or 4.

If the system has a user display, the dew point (or alternatively, the absolute humidity, or both dew point and absolute humidity) can be displayed rather than the chamber outlet temperature. As outlined above, the chamber outlet temperature can be an inaccurate indication of the humidity level of the gases exiting the humidifier chamber. This has been experimentally verified with a modular system substantially similar to that of FIG. 2. Data was measured over a full range of flow rates, from approximately 15 liters/minute to approximately 45 liters/minute. The chamber outlet temperature and the dew point at the chamber outlet formed part of the measured data. The data was measured for one substantially constant ambient temperature (although this was also measured throughout the test to remove uncertainty). The data collected is shown graphically in FIG. 8a and FIG. 8b, which show flow rate on the Y-axis against time on the X-axis. In the graph of FIG. 8a, the data was gathered for conditions of high ambient temperature. The measured flow rates are shown on the graph by the points 801. Line 802 shows the ambient temperature. Line 803 shows the measured chamber outlet temperature. Line 804a shows the measured dew point (Td measured). Line 805a shows the displayed dew point (Td displayed). As can be seen, the ambient temperature remains substantially the same (increasing slightly with time). The chamber outlet temperature changes from 39° C. to 41° C. The actual measured outlet dew point fluctuates around a substantially constant level. However, these fluctuations or variations mostly occur during flow transitions. The displayed dew point remains constant for the entire flow range.

Figure 8B:
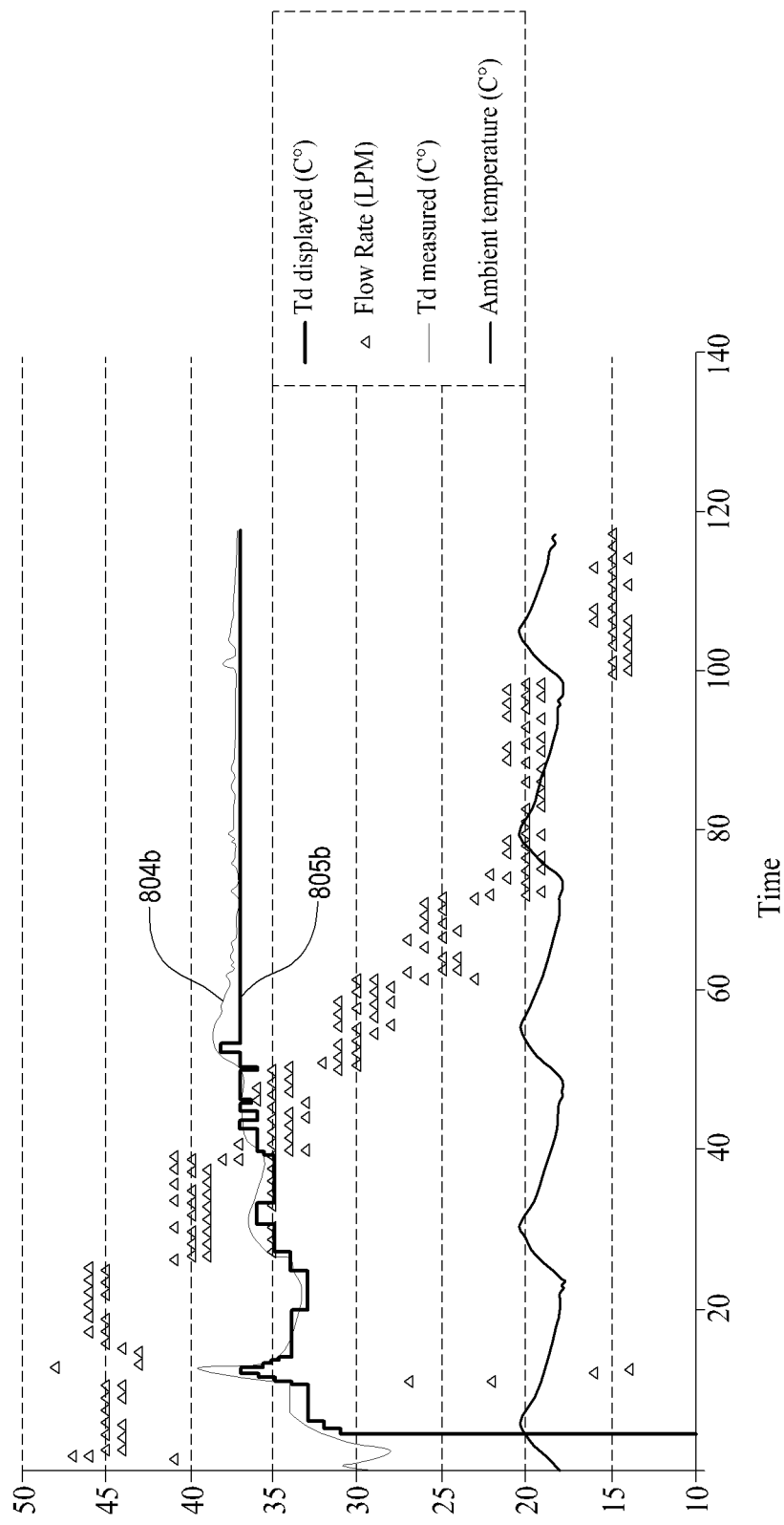
FIG. 8b shows a similar graph to FIG. 8a, for conditions of low ambient temperature.

FIG. 8b shows a similar graph to FIG. 8a, but for conditions of low ambient temperature (that is, 18-20° C.) and flow rates over the range 45-15 Liters/min. The chamber outlet temperature is not displayed as it is very close to dew point. It should be noted that in the preferred form, dew point is displayed when the temperature reaches 30° C. only. Patients should not use the humidifier when humidity is too low. It can be seen that ambient temperature oscillations have caused transient behaviour to appear in the measured dew point. However, despite this, the displayed dew point (Td displayed) as shown by line 805b can be seen to be 'tracking' the actual dew point (Td measured as shown by line 804b) very consistently. It should be noted that at 12 minutes, the flow rate was turned briefly from 45 Liters/min to 15 Liters/min, causing a small overshoot, as can be seen on the graph of FIG. 8b. At high flows of 45-40 Liters/min, the heater plate could not maintain the targeted temperature and the humidity output was lower than Td 37° C. This is reflected in the displayed dew point.

Further preferred variations and embodiments will now be described, which add to the improved control of the gases characteristics.

Further Alternative Sensor Layouts

In a variant of the apparatus and method outlined above, the system (system 1 or system 100 or system 200) also has additional sensors as outlined below.

1) A patient end temperature sensor 15 (or 115 or 215) is located at the patient end of the delivery conduit 6 (or alternatively in or on the interface 7). That is, at or close to the patient or point of delivery. When read in this specification, 'patient end' or 'user end' should be taken to mean either close to the user end of the delivery conduit (e.g. delivery conduit 6), or in or on the patient interface 7. This applies unless a specific location is otherwise stated. In either configuration, patient end temperature sensor 15 can be considered to be at or close to the user or patient 2. The reading from the patient end temperature sensor 15 is fed back to the controller 8 and is used to ensure that the temperature of the gases at the point of delivery substantially matches the target patient temperature of the gases at the chamber exit (the target patient temperature is the target dew point temperature at the chamber exit). If the reading from the patient end temperature sensor 15 indicates that the gases temperature is dropping as it travels the length of the delivery conduit 6, then the controller 8 can increase the power to the conduit heater wire (shown as wire 75 on FIG. 2a—not shown but present in the alternative preferred forms of breathing assistance system 200 and 400 shown in FIGS. 3 and 4, and the system shown in FIG. 2b) to maintain the gases temperature. If the power available to the conduit heater wire 75 is not capable of allowing the gases at the point of delivery to equal the dew point temperature at the chamber exit 9 then the controller 8 lowers the target chamber exit temperature (to lower the dew point temperature). The controller 8 lowers the chamber exit temperature to a level at or close to the maximum gases temperature the conduit heater wire is able to deliver to the patient as measured by the patient end temperature sensor 15. The controller 8 is loaded with a predetermined data set, and adjusts the power to the heater plate, or the conduit heater wire, or both, by using this data (which is similar to that shown in graphical form in FIG. 5). For a constant flow level and for a measured ambient temperature as measured by ambient temperature sensor 60 (which may change), there is an ideal patient end temperature. The controller 8 adjusts the power output or outputs of the heater plate and the conduit to match the temperature at the patient end of the conduit (as measured by temperature sensor 15) with this ideal temperature.

The above method can be further refined for accuracy if other conditions of the gases in the system are known—the gases conditions. For example, if the humidity level of the incoming gases to the blower is known, or the gases pressure of the incoming gases. In order to achieve this, alternative embodiments of the systems 1, 100 and 200 described above can also have a gases condition sensor located in the incoming gas path (e.g. a humidity sensor or a pressure sensor). For the modular system 1, a humidity sensor 50 is shown located proximal to the atmospheric inlet 40. For the integrated system 100, this is shown as humidity sensor 150 (and so on). In a similar fashion to the control methods outlined above, the controller 8 is pre-loaded with a humidity level data set. For a constant flow rate, and known ambient or external humidity level, there is an ideal gases temperature at the chamber exit (or at the point of delivery to a user). The data set contains these ideal values for a range of ambient humidities and flow rates, similar to the values shown in graphical form in FIG. 5. The controller 8 adjusts the power output of the heater plate, or the heater wire, or both, to match the measured chamber exit temperature (or patient end temperature) with the 'ideal' temperature retrieved from the data set in the memory of the controller). In a similar manner, the above method can be refined for accuracy if the pressure level of the incoming gases to the humidification chamber blower is known, locating a pressure sensor in the incoming gas path to the humidification chamber (pressure sensor 80 shown in the incoming gases path in FIG. 2 for the modular system. Pressure sensor 180 is shown in the incoming gases path in FIG. 3 for the integrated system. Pressure sensor 280 is shown in the incoming gases path in FIG. 4 for the central gases source system). It should be noted that if the data for the data set was plotted graphically for conditions of constant flow, ambient temperature and another gases condition (e g humidity or pressure), the graphs would be required to be plotted on three axes—X, Y and Z—the graphs would be 'three-dimensional' when plotted.

A further variation on the layout or construction of the breathing assistance system is as outlined below:

It is intended in some embodiments that the gases exit the chamber at 41° C. As the gases pass along the main delivery tube or conduit towards the interface, they are heated from 41° C. at the chamber exit to 44° C. at the end of the main delivery hose 6. At the end of the main delivery hose the gases enters a smaller secondary, unheated delivery hose—e.g. 6a as shown on FIG. 2b. As they pass through the secondary hose 6a the gases cool from a temperature of 44° C., to 37° C. as they enter the user interface 7. 37° C. is considered to be the optimum delivery temperature for the patient.

A further refinement of the method outlined above, with or without the additional sensors, will now be described.

Compensating for Convective Heat Loss and Heat Gain of Flow Generators

As outlined in the prior art section, one problem that is known in the art is that of accurately controlling the output characteristics of a system when there are a large number of variables which can affect the output characteristics. It has been found that one of the variables that has an effect on the gases output characteristics is convective heat loss from the humidifier chamber 5. This convection can be caused by natural factors such as temperature gradients in the room—"natural or free convection" or by forced movement of air—"forced convection". Forced convection could for example be caused by a ventilator or an air conditioner. Convection cooling of the humidifier chamber can substantially affect the dew point temperature at the humidifier chamber outlet. A flow of air over the outside surfaces of the humidifier chamber—e.g. chamber 5 of system 1—will cause the temperature inside the chamber to drop. In order to compensate for this, more power is required at the heater plate to increase the temperature of the contents of the chamber 5. The output temperature at the chamber outlet is measured by outlet temperature sensor 63, and the temperature loss will be 'seen' by the controller 8 as it records a drop in temperature at the chamber outlet. The controller 8 will increase the power to the heater plate 12 to compensate for this (with a corresponding increase in heater plate temperature measured by the heater plate temperature sensor 62). The effect of this increase in power is to increase the heat transfer ratio from water to gas and the partial water pressure of gas inside the chamber, and consequently there is an increase in the dew point temperature.

Evaporation of non-boiling water is governed by Low Mass Transfer Rate Theory and mass (water) transfer directly related to heat transfer. So the evaporation depends on the temperature of the incoming gas (and less so on its humidity), temperature of water, flow and pressure. Flow determines not only flow of gas over water but also the movement of water. For example, stirring (forced convection) of water will increase the evaporation. The evaporation rate is higher during a transition mode of a heater plate controller. The transition mode is characterized by larger oscillations of temperature in the heater plate and likely causes an increased turbulence (free convection) in water by raising the Nusselt number and its mass transfer analogue the Sherwood number. This is more noticeable at high ambient temperature, or more particularly under conditions where gases entering the humidifier are at a high temperature, and when chamber outlet gas temperature is significantly higher than dew point. Convective heat loss causes dew point to increase close to the temperature of the gas.

Elevated chamber outlet temperature over dew point causes instability in the control system. Any fluctuations of flow or convective heat loss will cause a quick increase in mass (water) transfer and subsequently humidity of the gas. This instability is illustrated in FIG. 8a where measured dew point (804) of the air at high ambient temperature cycles while measured temperature at the chamber outlet (803) remains relatively stable.

Figure 1:
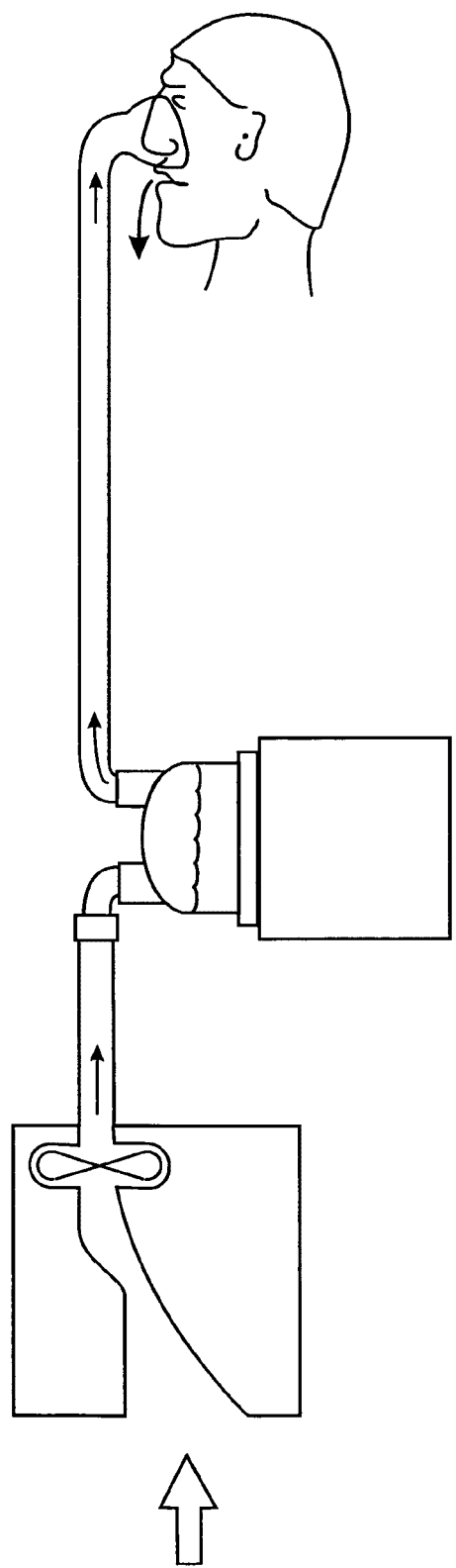
FIG. 1 shows a schematic view of a user receiving humidified air from a modular blower/humidifier breathing assistance system of a known, prior art, type.

This is a typical problem of humidity output control in respiratory support devices that have incorporated both a flow generator and humidifier (such as CPAP blower, BiPAP or non-invasive ventilators etc—see FIGS. 1, 2 and 3 for example) and have a typically targeted dew point at 31-32 degrees, rather than dew point close to a body temperature of 37° C. (high humidity with dew point 37° C. is typically used in high flow therapy and invasive ventilation).

The flow generator will cause the temperature at the chamber inlet to be increased above usual ambient temperature (22-24° C.) by several degrees. The inlet temperature may become very close to or even exceed 31-32° C. Increased ambient (atmospheric) temperature significantly aggravates the problem. The increased chamber inlet temperature requires air to be heated to approximately 36-41° C. or even higher (depending on the flow rate) to achieve a dew point of 31-32° C. The patients' physiological breathing or mechanical ventilation may also affect flow in the humidification chamber and as a result exposure time of air in the chamber. All these conditions combine to produce variable humidity output at the chamber outlet. If the humidification chamber is exposed to environment, which is usually the case for practicality, the convection heat loss can also significantly alter the humidity output.

The convective heat loss ('draft') is created by airflows over and around the ventilation equipment, and particularly the humidifier chamber. This can be particularly significant in designs where the chamber is at least partially exposed, particularly in ventilated spaces. The flow velocities of the air vary in magnitude, direction and fluctuation frequency. Mean air velocities from below 0.05 m/s up to 0.6 m/s, turbulence intensities from less than 10% up to 70%, and frequency of velocity fluctuations as high as 2 Hz that contribute up to 90% of the measured standard deviations of fluctuating velocity have been identified in the occupied zone of rooms.

The convective heat loss can also be estimated by measuring flow intensity or turbulence intensity (or both) over the chamber. This can be achieved using thermal, laser or sonic anemometry, with sensors mounted on the equipment (e.g. the humidifier base unit 21) so as to measure the flow or turbulence intensity at or close to the humidifier chamber 5.

For precision humidity control, compensation for convective heat loss is desirable. This compensation is made easier if the controller 8 has the advantage of a 'convection compensation' data set or sets to rely on, or if the controller has the advantage of an alternative 'convection compensation' method. The controller could be programmed with a fuzzy-logic type rule-based system.

The data set shown graphically in FIG. 5 is calculated under conditions where there is little to no convective heat loss. This data is suitable for use under conditions where there is low movement of the ambient air. In alternative forms, or variants of the apparatus and method outlined above, the controller 8 will switch to using alternative data as input when the convective heat loss reaches a certain level—for example, if the controller 8 notes a large step change in the heater plate temperature as measured by the heater plate temperature sensor 62. For example, the data will be used as input for a fuzzy logic control algorithm, a mathematical formula or formulae, or similar.

Figure 6:
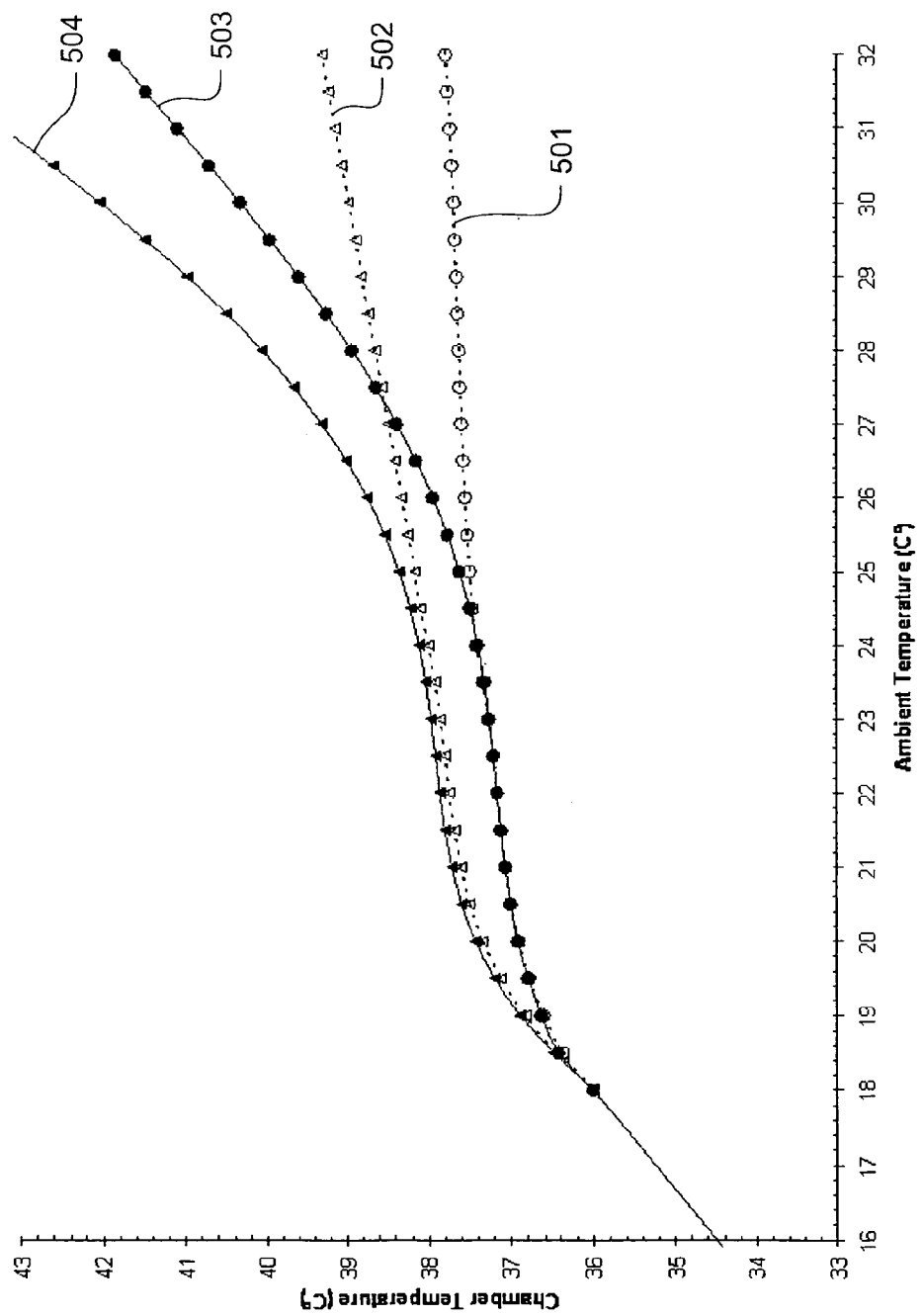
FIG. 6 shows a graphical representation of an alternate data set for use with the breathing assistance system of FIG. 2, 3 or 4, the alternative data compared to or used alongside the equivalent data from the table shown graphically in FIG. 5, the graph lines showing curves representative of two different steady flow rates for a range of ambient atmospheric temperatures with little movement of the ambient air, and a range of target temperatures for a given flow and ambient temperature, and the same steady flow rates shown over a range of ambient temperatures with high convective heat loss from the humidification chamber, the data from the look-up table loaded into the system controller in use.

FIG. 6 shows part of the data for use if or when ambient conditions change during use to a 'high convection' condition—if during use there is a flow of air over the apparatus, and in particular the humidifier chamber, and as a consequence there is a change from a low convective heat loss condition to a high convective heat loss condition. The alternate data of FIG. 6 is created in the same way as the table shown in FIG. 5, but the pre-measured and pre-loaded conditions (flow and ambient temperature) are for a system where at least the chamber 5 (or 105 or 205) is experiencing a high level of convective heat loss. The target temperature changes accordingly. In FIG. 6, part of the alternative data for use in a 'high convective heat loss' condition is shown. Two curves 501 and 502 are shown, representative of a steady flow rate of 15 liters/minute (501) and 45 liters/minute (502). A range of ambient temperatures (X-axis) and a range of target chamber exit temperatures for a given steady flow rate and ambient temperature are shown (Y-axis), in a similar manner to the data shown in FIG. 5. For the purposes of comparison, the two equivalent steady flow lines (15 liters/minute and 45 liters/minute) from FIG. 5 are also shown on the graph as lines 503 (15 liters/minute) and 504 (45 liters/minute). It can be seen that when the apparatus is subject to a 'high-flow' condition, the target chamber outlet temperature as shown on the Y-axis is lower than when the apparatus is subject to a low-draft' or low level of convective heat loss condition.

Similarly, alternate rule sets can be calculated and pre-loaded into the controller 8. The controller can switch between alternate fuzzy logic rule-sets depending on the ambient conditions as measured or assessed by the methods) outlined above—for example when the convective heat loss reaches a certain level assessed by the controller 8 noting a large step change in the heater plate temperature as measured by the heater plate temperature sensor 62.

In order for the controller 8 to assess whether it should be using data representative of low convective heat loss or high convective heat loss, an assessment of the heat loss is required. In the preferred embodiment, this is calculated from the power required at the heater plate 12 to maintain the correct chamber exit temperature. The controller 8 is pre-loaded with data values of heater plate power for known ambient temperatures and flow rates (alternatively the controller utilises fuzzy logic rule sets). The controller 8 assesses whether the humidifier chamber is operating in a condition of high convective heat loss, or a condition of low convective heat loss, and adjusts or alters it's control output accordingly (e.g. by utilising the fuzzy logic rule sets to change operating condition). The condition of 'highest convective heat loss' is defined as the condition (fast moving air) when the controlled chamber outlet temperature is close to dew point and further cooling of the chamber does not increase the humidity. 'Low convective heat loss' is defined as the condition (still air) when the controlled chamber outlet temperature is raised above the dew point temperature. This is explained further below:

Normally the controller 8 uses an algorithm or rule set of 'low convective heat loss' (still air, or low convective heat loss). When the chamber 5 is cooled from outside by convection ('high convective heat loss') the humidity output will increase. The target chamber outlet temperature for the method outlined above (i.e. using the data shown in FIG. 5) uses look up table data (or a rule set) that corresponds to a heater plate temperature range and/or duty cycle of the heater plate. The controller 8 will switch to data representative of 'high convective heat loss' if a target value of the chamber gas outlet temperature is reached and the corresponding heater plate temperature is higher than a set limit for a given time period (this change could also be incorporated as one of the rules in a fuzzy logic rule set). It should be noted that if a system is used that does not have a heater plate temperature sensor, the heater plate power duty cycle can be used instead of the heater plate temperature to calculate the switchover point—that is, if a target chamber gas outlet temperature is reached and the power drawn by said heater plate is higher than a set value for a given time period.

The controller 8 will decrease the target chamber gas outlet temperature by an appropriate value.

Example

In the preferred embodiment, for the system 100 of FIG. 3, if a target value of 39.5° C. of the chamber gas outlet temperature is reached and the corresponding heater plate temperature (or calculated power) is higher than 60-65° C. for five minutes, the controller 8 will determine a control output that decreases the target chamber gas outlet temperature by 0.25° C.

This new value also has a new corresponding heater plate temperature and/or duty cycle (i.e. chamber gas outlet temperature 38.4° C. and heated plate temperature 87° C.). So, the targeted dew point temperature is titrated until it has proper corresponding heated plate temperature (by a fuzzy logic algorithm in the controller 8). If the heater plate temperature is significantly higher than the corresponding chamber gas outlet temperature then the new targeted value is approached quicker. For example, if the heater plate temperature is more than 10° C. higher then the new targeted value is reached in less time (i.e. 0.5° C. lower) etc. This drop of the targeted chamber gas outlet temperature may vary according to flow and/or ambient/gas chamber inlet temperature. For example, at a flow rate of 45 Liters/minute and an ambient temperature of 23° C. this drop can be of 0.1° C. for every 5° C. of heater plate temperature. At an ambient temperature 30° C. it can be 0.7° C. for every 5° C. of the heater plate temperature. Moreover, the drop of the target temperature can be non-linear.

In alternative embodiments, the heater plate temperature, the heater plate duty cycle, the heater plate power, the duty cycle of the heated tube, or the heated tube power can be used for estimation of the convective heat losses. The heated tube has a larger surface area and will therefore react quicker to convection changes.

The same principle as outlined above is applied in reverse when the convective heat loss is decreasing after it has increased. Time limits and steps of the chamber gas outlet temperature increase or decrease may vary.

The displayed dew point can be corrected in a way that tracks actual dew point during the transition time.

In other alternate embodiments, multiple sets of data can be used for different levels of convective heat loss, with the controller 8 using one, some or all of the data sets to determine the control output for different convective heat loss ranges, for example by using fuzzy logic control algorithms, mathematical formulae or similar.

In yet another alternative embodiment, the use of multiple data sets can be avoided by using a single data set, and modifying the target chamber outlet temperatures as follows. If the flow rate, the ambient temperature and the heater plate power use or heater plate temperature are known, the target chamber outlet temperature can be modified according to the (known and changing) level of heater plate power. (or temperature) for any given ambient temperature and flow rate. In this way, the level of 'draft' or convective heat loss, for example, can be calculated from heater plate power used. The target chamber outlet temperature is modified to provide accurate dew point control for a range of convective heat loss conditions, by applying a correction factor or correction algorithm to the data in e.g. the data set used to create the graphs of FIG. 5. For example, if using heater plate power, the calculation can be made as follows: The required heater plate power for any given target chamber outlet temperature and flow rate for low convective heat loss conditions is known, and these values are stored in the memory of the controller 8. In use, the controller 8 receives data relating to the power used by the heater plate, and compares this to the stored data. If the measured data values and the stored data values are not substantially similar (within +/−2% in the preferred form), the controller applies an inversely linear correction factor. For example, if the measured heater plate power is 10% greater than the stored values (indicative of a high convective heat loss condition), the controller decreases the target chamber outlet temperature by 10%.

It should be noted that heater plate temperature or any of the other methods outlined above (e.g. heater plate temperature, conduit power, etc) could be used instead of the heater plate power as outlined in the example above.

In a similar fashion, if one or more of the conditions of the gases is known, then a correction algorithm or correction factor can be applied to the (ambient condition) data stored in the memory of the controller 8. The ambient conditions under which the data was measured and loaded are known (e.g. humidity and pressure). If the measured gases condition deviates from these base line conditions by a certain percentage (e.g. more than 2%), then the controller can apply a correction factor to the target chamber outlet temperature.

Figure 12:
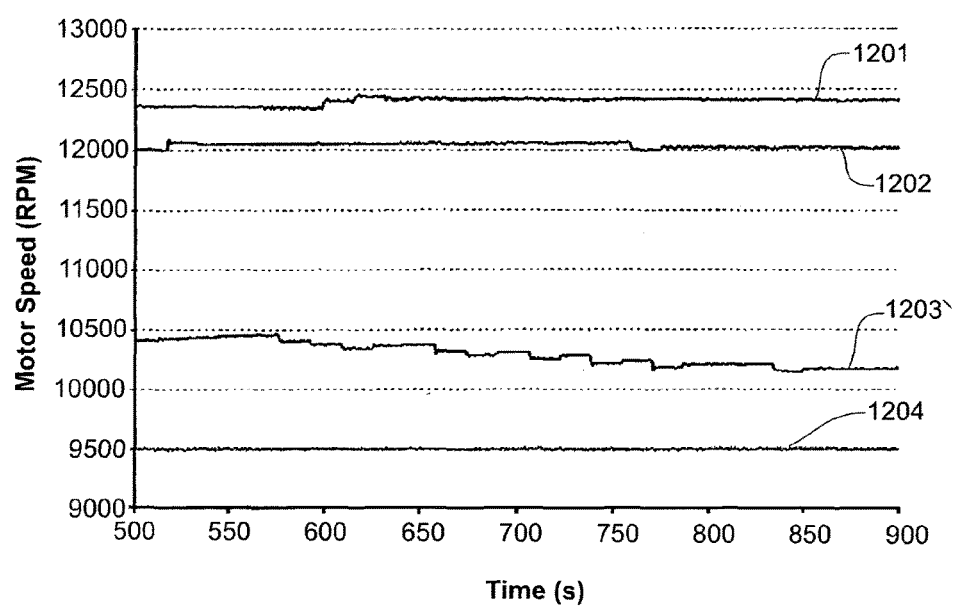
FIG. 12 shows a graph of motor speed for a number of example interfaces, demonstrating that humidity can be controlled to an appropriate level for either a mask or a nasal cannula (which require different motor speeds, with the system remaining stable and producing an appropriate humidity level at both high-speed and at low-speed).

In the embodiments of a coupled blower and humidifier presented schematically in FIGS. 1, 2 and 3, the chamber inlet temperature will usually be augmented with an increase of flow, or pressure, or both, from a flow generator. A fuzzy logic algorithm or algorithms can be used to define the corrected chamber inlet temperature according to ambient temperature or chamber entry/inlet temperature, and motor speed. An increase in the motor speed is usually accompanied by an increase of the chamber inlet temperature. Furthermore the known motor speed can be used by the controller for defining humidity and temperature regimes according to a known interface attached at the patient end of the delivery conduit. For example, the lower motor speed associated with a mask interface (as opposed to a nasal cannula) can be used in the algorithm to control humidity output from the system to an appropriate level for a mask. When a mask is used, a dew point of 31° C. is required. A small or large nasal cannula, or a tracheostomy fitting, require a dew point of 37° C. This is shown in FIG. 12, which shows a graph of motor speed for a number of example interfaces—a higher fan RPM is required for nasal cannula applications, and a lower fan RPM is required for mask applications. The RPM output of the motor can be kept more stable by using the control method outlined above. The experimental results shown in FIG. 12 demonstrate that humidity can be controlled to an appropriate level for either a mask or a nasal cannula (which require different motor speeds, with the system remaining stable and producing an appropriate humidity level at both high-speed and at low-speed). The x-axis shows time in use (in seconds). The y-axis shows motor speed (RPM). Line 1201 shows the motor speed for the system in use with a small nasal cannula. Line 1202 shows the motor speed for the system in use with a large nasal cannula. Line 1203 shows the motor speed for the system in use with a tracheostomy interface. Line 1204 shows the motor speed for the system in use with a mask.

There are other potential ways m which the delayed 'self heating' effect of the blower as it gradually warms up or heats up during use can be compensated for.

Firstly, after a period of time of steady work (e.g. one hour, two hours, etc), the humidity control algorithm can switch from using the chamber outlet temperature as a variable, to using the heater plate temperature.

Secondly, a time component can be implemented in the control algorithm (e.g. after one hour of work the target chamber outlet temperature can be increased by e.g. 0.5° C.

Thirdly, "the heat-up compensation factor" can be used. This factor can be calculated using: time of work, duty cycle of heater, and heater plate temperature. If the duty cycle or heater plate temperature changes over time, under conditions of steady flow rate and ambient temperature, then this indicates that the air coming from the blower is becoming hotter with time, and this has to be compensated for.

Control for Constant Flow Rate

In the most preferred forms of the invention, the systems 1, 100 or 200 also have a flow control system, which is adapted to control the flow through the system and keep this aligned as closely as possible to the desired, user set, level. As outlined above, the flow and the humidity of the gases in the system are interlinked. As outlined above, in prior art systems, it is normal for the fan to be set to a constant speed, and it is assumed that the flow rate will remain substantially constant if the fan speed remains constant, or that the pressure at the point of delivery to the patient is constant. However, the flow can be affected by changes in the system (which affects the humidity), even if the power to the fan remains constant, or the fan speed remains constant. This is especially true if the conduit, or interface, or both, have a relatively low resistance to flow. The difference or deviation between the magnitude of the measured or actual flow against the magnitude of the user-set flow can be characterised as a 'large deviation' or a 'small deviation'. In the preferred embodiment, the difference between the actual flow rate and the desired (user-set) flow rate determines whether the controller 8 uses fine control or coarse control to match the actual flow rate to the desired flow rate.

For example, in the preferred form of system 1, when the system is first turned on or activated, it 'warms up' prior to use. As it warms up, the flow rate approaches the user set point. A user will generally not be wearing their interface during the warm up period, and the interface may not be connected to the delivery conduit. When a user puts their interface on, or connects the interface to the conduit, the flow rate will decrease as the resistance to flow will increase. This can cause a user discomfort. Other unwanted side effects can also occur—for example a change in the concentration of oxygen delivered, or a change in the delivered humidity. The change in flow rate due to the increased resistance to flow will be large or a large proportion or percentage of the overall flow rate, and can result in a large deviation of the measured flow from the user set flow. Another example of a large flow deviation would be for example if the user interface is changed or swapped e.g. from a full face mask to a nasal mask or a nasal cannula. There will be a change in the flow rate that may be characterised as a large deviation from the user set flow—the difference between the measured flow and the user set flow will be large. Large deviations can also occur if e.g. small-bore nasal cannulas are swapped for large-bore cannulas.

In contrast, there are changes to the flow rate through the system that can be characterised as 'small deviations'. Some examples of changes to the system which cause 'small deviations' from the user-set flow rate are as follows: If the geometry of the delivery conduit changes (e.g. if a user turns over in their sleep and alters the way the delivery conduit is flexed or bent), then there will be a small relative or small change or percentage change in the flow rate, and the deviation of the actual flow rate from the user set flow rate will also be small. Small deviations from the user set flow may also occur for example if the position of the user interface on the user's face or in their nostrils changes.

For the purposes of this specification, a base flow rate is set as follows: by the user defining the 'user set flow rate'. The flow rate through the system is measured, continuously or periodically giving the 'actual flow rate' (e.g. via the flow probe 61). As long as the actual flow rate as measured matches the user set flow rate to within a predefined tolerance—e.g. 3 liters/minute, the controller 8 characterises the flow rate as within tolerance—that is, there is not a 'large deviation' between the actual measured flow rate and user set flow rate. If the measured flow rate is different from the user-set flow rate by more than the predefined tolerance of 3 liters/minute or more from the set base flow rate, the controller 8 characterises this as a 'large deviation' in a similar manner to that outlined above. In contrast, if there is a difference between the measured flow rate and the user-set flow rate that is smaller than 3 liters/minute, this is characterised as a small deviation. It should also be noted that in alternative embodiments, the controller could work from a percentage deviation from the user set flow rate, rather than an empirical change such as the 3 liters/minute of the preferred embodiment described above.

In the preferred embodiment, the control system or control algorithm loaded into the controller 8 is designed to switch between coarse control and fine control, depending on whether there has been a large deviation or a small deviation. If the controller 'sees' a large deviation or a step change in the flow rate, it uses coarse control parameters to restore the flow rate to the rate set by a user. If the flow rate is changing slowly, or if there is a small deviation in the flow rate, the controller 8 uses fine control parameters to adjust the flow rate.

To avoid system or measurement deviations associated with noise or with a patient breathing on the system triggering coarse control, the actual measured flow used is an average flow calculated over a period of time greater than a few breath periods, rather than the instantaneously measured flow.

A pre-loaded control system or systems (or a control algorithm or algorithms, or fuzzy logic rule set) which is incorporated as part of the controller 8, and which acts on the system 1 (or 100, or 200) to smooth the flow rate with the aim of delivering constant flow to a user undergoing humidification therapy is useful as it allows the flow to be set, and known. The flow is independent of the interface being used, the fit of the interface on a user, and the depth of the users breathing. This is particularly useful if a user is undergoing $O_2$ therapy for example by using the system 200. If the flow of $O_2$ provided by e.g. a central gases supply (provided to the humidifier chamber via a wall inlet and conduit) is known (measured by the flow probe), and the flow rate from a separate atmospheric supply is known (either measured by a separate flow probe, or calculated from the system dimensions (e.g. the venturi dimensions) and the measured flow rate, using an algorithm in the controller), then a look-up table loaded in the controller 208 can calculate the $O_2$ fraction in the blended humidified air. For example, the difference in airflow between a cannula interface and a trachea interface is typically 5 liters/minute or greater for the same user. If the separate flow rates from atmosphere and the central supply are known, the $O_2$ fraction can be set via user controls 11 to known values for either of these interfaces without the need for an $O_2$ sensor. Also, by having a system that has a flow sensor which feeds back to the controller 208 and which sets the flow irrespective of the interface or breathing pattern of the patient, the humidity can be precisely controlled as outlined herein. Therefore, with a preset flow the breathing assistance system can deliver precise oxygen fractions and humidity without the need for an oxygen sensor or humidity sensor. Precise flow control enables precise delivery of blended oxygen. Precise flow control also enables precise control of the humidity levels in the gases (for example blended oxygen) delivered to the patient.

Figure 9:
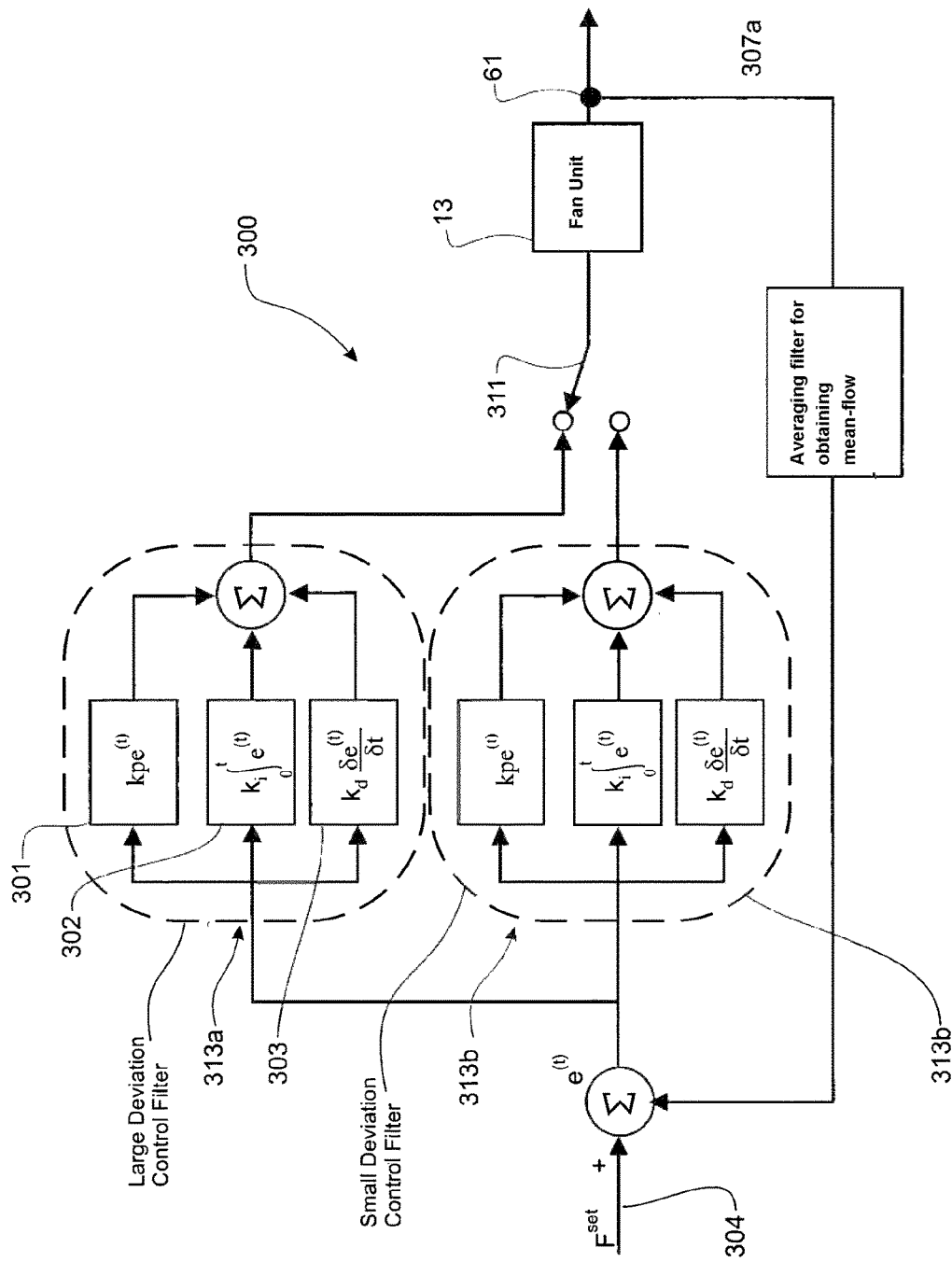
FIG. 9 shows a schematic representation of part of the programming for a control system that is used by the breathing assistance System of FIG. 2 or FIG. 3 to adjust the flow rate through the system so that it remains substantially constant when the geometry of the system changes, the control mechanism containing two P.I.D. control filters, one for large deviation and one for small deviation from the set flow rate, the control mechanism also containing an averaging filter located in a feedback path to compare the measured flow with the set flow rate.

A schematic diagram showing the operation of a control system 300 is shown in FIG. 9. In the preferred form, the controller 8 (or 108 or 208) is loaded with a control system 300. The controller 8 uses P.I.D. control algorithms from a P.I.D. filter 313 as the coarse control parameters or large deviation control parameters. In the filter 313, the 'P' or proportional part is shown as 301, the 'I' or integral part is shown as 302, and the 'D' or derivative part is shown as 303. In the control sub-system or algorithm, the fan unit 13 is shown, with the flow probe 61 shown downstream of the fan unit 13. User input from the controls 11 is shown as arrow 304. A feedback signal 307*a* is shown from the output of the control system or sub-system back to the front or input end, to be fed into the filter 313 along with a signal indicative of user set flow rate—user input 304 (it should be noted that when the phrase 'user set flow rate' is used in this specification, it can be taken to mean the user input signal 304). Arrow 311 shows the input into the fan unit 13, which is the output or signal from the P.I.D. filter 313 (either large deviation control filter 313*a* or small deviation control filter 313*b*).

It can be seen from FIG. 9 that the filter 313 is divided into a 'large deviation control filter' (313*a*) and a 'small deviation control filter' (313*b*). The controller 8 switches between the two filters depending on the parameters outlined above.

It should be noted that the coarse flow control or 'large deviation' control can be achieved by using heater plate temperature, or tube temperature, or both, as the input. If the temperature changes above a certain rate of change (a large deviation), then the controller initiates coarse control. The controller could also use the power or duty cycle of the heater plate or heater wire (or both), and the using a look-up table, formula or fuzzy logic algorithm. (this flow control can be used as a stand alone or as a back-up control system). It may not be accurate enough for oxygen therapy but can be potentially implemented in surgical humidification or high flow therapy (without $O_2$).

Also data from the oxygen sensor (air enriched with $O_2$) can be used as an input for fuzzy logic of flow control (change of $O_2$% may reflect flow change)

The flow control method and system described above can be further refined to control the flow rate during the inspiration-expiration cycle, as described below.

Intra-Breath Control.

The flow control method described above addresses average flow—i.e. mean flow over a time period greater than that of a number of breathing cycles (e.g. three or more inspiration-expiration cycles). There is a need for the implementation of a control system for maintaining constant flow over the course of a breath (inspiration/expiration). A preferred manner in which this could be implemented is described below.

Flow through the conduit will vary as a patient inhales and exhales (i.e. over the course of a single breath or breathing cycle). The percentage amount by which the flow will vary over the course of a breath depends on a number of factors—for example the resistance of the tube/interface combination, the leak or seal around the cannula in the flares and the size of the breath taken. A very high resistance conduit and cannula combination is unlikely to need a control system for maintaining constant flow over the course of a breath. However, a low resistance interface such as a nasal cannula for use with the system 1, 100, or 200 is more likely to need a control system—the variation in the flow can be relatively large.

In some circumstances flow variation may actually be beneficial—it may reduce the work required by a user to breathe, and may be more comfortable for a user as the pressure at the nose during expiration is lower than it would otherwise be for a constant flow device. In other circumstances it may be beneficial to have a more constant flow through the tube. This will give a greater pressure during expiration and cause higher PEEP. This is useful and advantageous for treating some respiratory ailments. For a relatively low resistance tube (and low back pressure of the blower) the change in flow between inspiration and expiration can be relatively large, for example 5 L/min or more.

The change will be greater when the user set flow is relatively low. Controlling flow during breathing is generally more difficult than controlling average flow. This is because the time response of the motor used as part of the blower unit 13 is often comparable to breath rate. Care needs to be taken to ensure that the breathing system such as the breathing assistance system 1 will be stable at all operating conditions, but maintains a sufficiently fast response. This is done by careful choice of the control parameters. For example if a P.I.D. system is used the P, I and D gains must be set very carefully.

The intra-breath control method is implemented in the preferred form as follows, with reference to FIG. 10*a*.

Firstly, the flow is sampled at a rate that allows intra breath variations to be picked up. In the preferred embodiment, this sample rate is in the region of 25 Hz (e.g. 20-30 Hz—that is, the flow rate is measured by the flow probe 61 (or 161 or 261) between 20 and 30 times per second). The flow probe 61 used in the preferred form of breathing assistance system 1 must be able to respond to changes sufficiently quickly to achieve this response. As outlined above, P.I.D. control algorithms are pre-loaded for use in the controller 8. A problem with the D' or Derivative term 303*a* or 303*b* is that small amounts of measurement or process noise can cause large amounts of change in the output. In the preferred form of the present invention, in order to ensure the response is sufficiently rapid, this filter is not present. Alternatively, as shown in FIG. 10*a*, a low pass filter 321 with cut-off frequency high enough to allow intra-breath flow variation to pass unattenuated or nearly unattenuated is used. This increases the response time of the fine control system so that both the average and the intra breath variation will be compensated for. Care needs to be taken to ensure that the parameters of the control filter are chosen to ensure unwanted effects such as overshoot and oscillation that will cause the user discomfort do not occur over the entire range of flows used and for all patient interfaces used.

The system could also be used without the filter 321 present. However, removing this filter may require the use of a more accurate flow sensor. The gains used will have to be kept small enough to make sure that the noise does not adversely affect behaviour—this may result in a performance that is not ideal, e.g. the flow may not be as constant as one would like.

As outlined above, the controller 8 uses either fine or coarse control by constantly receiving input from the flow probe 61, which samples the flow rate between 20 and 30 times per second in the preferred embodiment. The instantaneous flow is used to calculate the average flow over a period of time greater than a few breath cycles using e.g. a low pass filter 320 which is used to calculate the deviation of the average flow from the user-set or desired flow. In the preferred embodiment, if the measured average flow is different by a preset value of e.g. greater than 3 Liters/minute from the user-set or desired flow rate, then the controller 8 uses coarse control parameters or 'large flow deviations' 313*a* to adjust the flow rate to the user-set level. If the average flow rate deviates from the average by a proportion of 15%, or more than 3 liters/minute, then the controller 8 or 108 initiates coarse control. Otherwise, fine control or small flow deviations 313*b* are used.

Figure 10A:
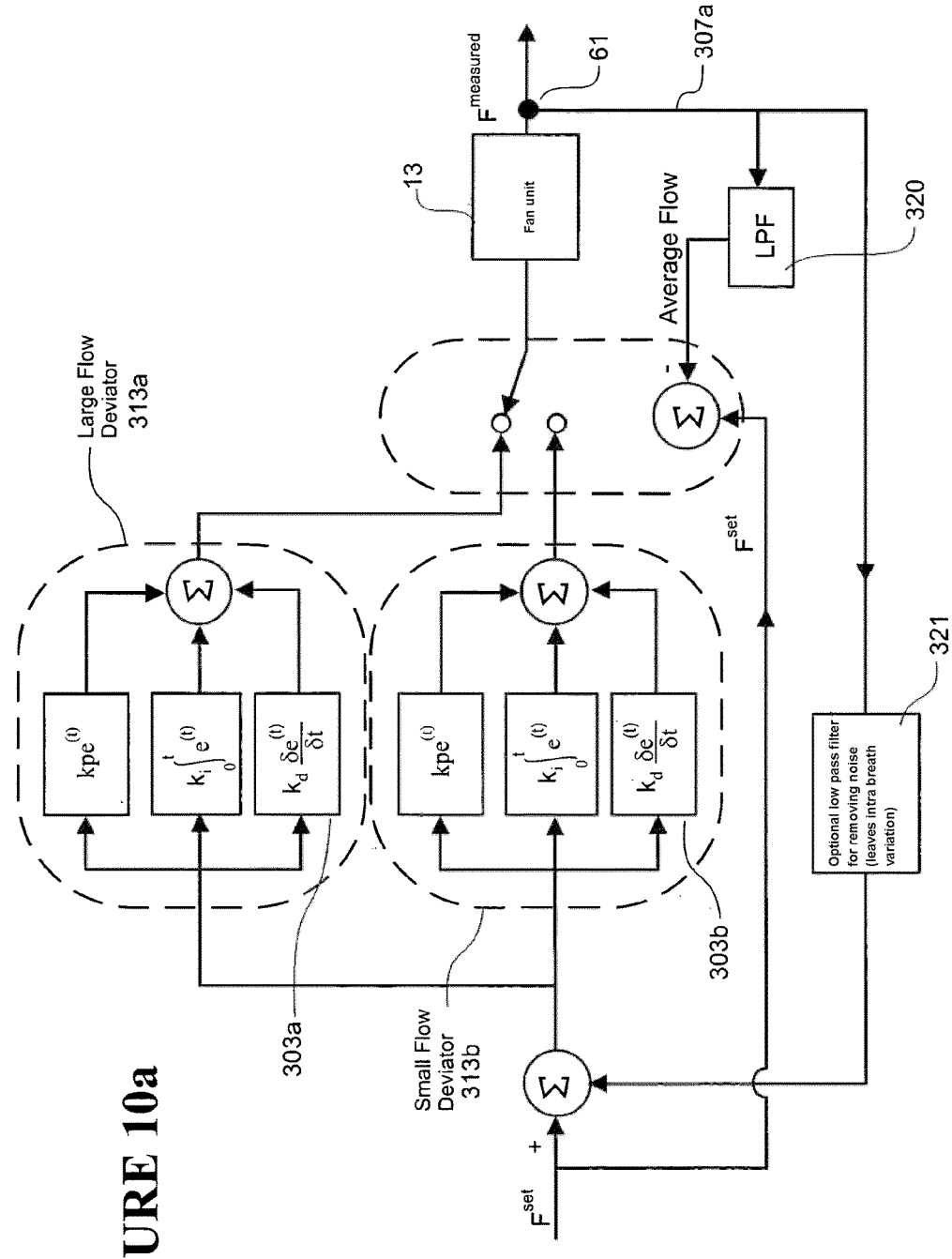
FIG. 10a shows a schematic representation of part of the programming for a control system that is used by the breathing assistance system of FIG. 2 or FIG. 3 so that average and intra breath flow can be controlled with a low-pass filter also incorporated as part of the programming and used for determining whether coarse or fine flow control is used.

In order to ensure that stable operation is maintained during coarse control the average flow obtained using the output of filter 320 can be fed back into the controller rather than the instantaneous measured flow shown in FIG. 10*a*.

Figure 10B:
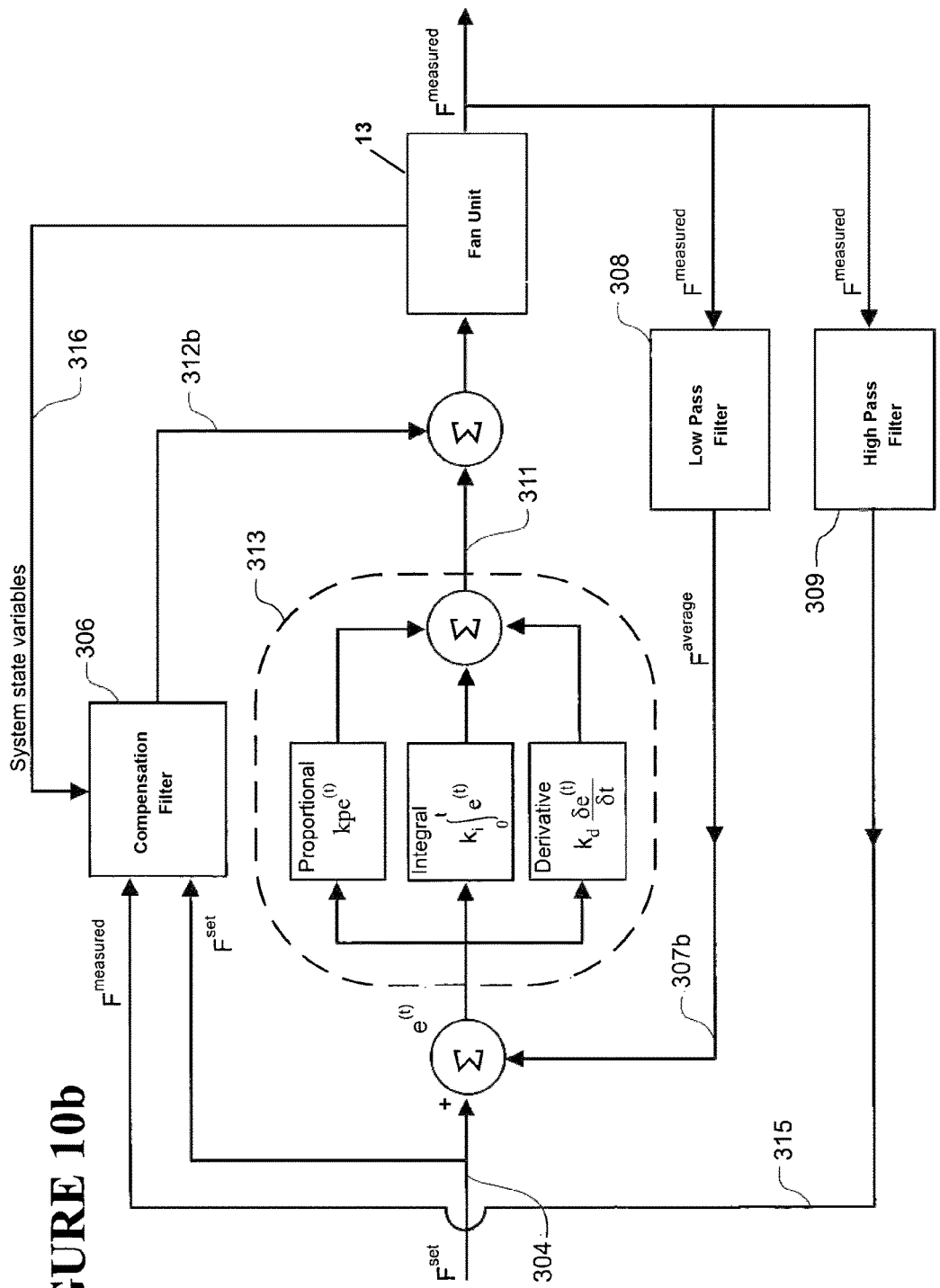
FIG. 10b shows a schematic representation of part of the programming for a control system which incorporates dual feedback loops for improved flow control in the system of FIG. 2 or FIG. 3, the dual feedback loops allowing separate control filters, so that average and intra breath flow can be controlled.

In a variant or second preferred form or embodiment, the controller 8 compensates for flow variation resulting from the breathing cycle by passing the signal 307a (the signal indicative of actual flow rate) in parallel through a low pass filter 308 and a high pass filter 309, as shown in FIG. 10b. The low pass filter produces an output signal 307b. The high pass filter 309 produces an output signal 315 that feeds back to a compensation filter 306. The output signal 311 from the P.I.D controller and the output signal 312a from the compensation filter 306 is used to control the speed of the fan in the fan unit 13. This has the advantage of allowing the P.I.D. filter 313 for the average to be set independently of the intra-breath control filter. This makes it easier to design a stable and robust control system.

The dual feedback loops shown in FIG. 10b allow separate P.I.D. gains, so that average and intra breath flow can be controlled. The decision as to whether to use fine or coarse control for the adjustment of the mean flow is made by examining the deviation of the output of the low pass filter, 307b, from the user set flow as described previously.

Yet another difficulty which is encountered with prior art systems, is that the breathing assistance system is a nonlinear system—the open loop gain to the system varies with the state of the breathing assistance system. That is, a given change in blower pressure or motor speed will produce a change in the flow rate that depends on the current state of the breathing assistance system. For example if the blower unit 3 is operating at a high flow rate condition, and the overall flow rate changes by a certain amount because the user exhales, the change in pressure or motor speed required to compensate for this change will be different than it would be if the blower unit 3 was operating at a low flow rate. This can cause problems with stability, and it is possible for prior art control systems to become unstable at some flow values or motor speeds. Also it is possible that the response time may become too slow to adequately compensate for intra-breath variation. This can be a particularly problematic in a system where the response time is similar to that of the disturbance, for example in systems where rate of flow variation is similar to the time response of the fan unit 13.

There are a variety of different controllers that can be modified to help overcome these effects. One way is to use a controller with a control filter with parameters that vary as a function of the state of the system. For example, if a P.I.D. controller is used the P, I and D parameters may not be constant but a function of the average (or even instantaneous) flow, or blower pressure or motor speed or of the user set flow.

Figure 11:
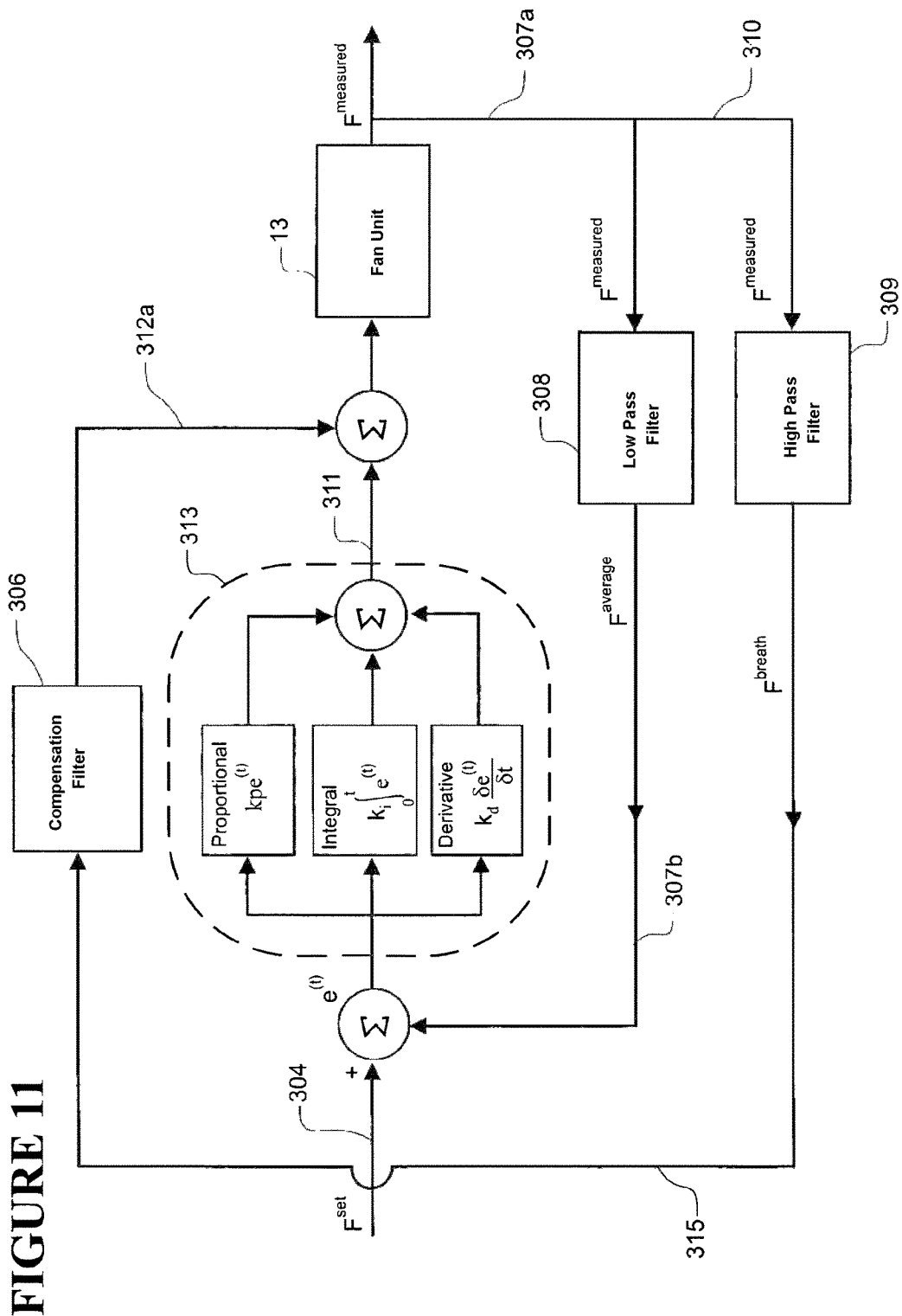
FIG. 11 shows a schematic diagram of the system of FIG. 10b, with the addition of a further feedback path from the flow generator to the compensation filter, to assist in compensating for the non-linear nature of the breathing system shown in FIGS. 2, 3 and 4.

FIG. 11 shows a schematic diagram of how this might be achieved. The control system is the same as that shown in FIG. 10 and as described above, but with the addition of a feedback signal 316 from the flow generator or fan unit 13 to the compensation filter 306. The input signal to the fan unit 13 in this variant will therefore be the output signal 311 from the P.I.D. filter 313, and the signal 312b from the compensation filter 306.

What is claimed is:

1. A breathing assistance system for delivering a flow of gases to a patient for therapeutic purposes, comprising:
    a humidifier unit comprising an inlet port and an exit port, said humidifier unit configured to hold and heat a volume of water, said humidifier unit further configured to permit a flow of gases to enter said humidifier unit via said inlet port, pass through said humidifier unit and become heated and humidified, and exit said humidifier unit via said exit port,
    an ambient temperature sensor configured to measure a temperature of said flow of gases before said flow of gases enters said humidifier unit,
    a conduit configured to deliver said flow of gases from said exit port to said patient via an interface, said conduit comprising a heater wire configured to heat said flow of gases within said conduit,
    a patient end temperature sensor configured to measure a temperature of said flow of gases close to said patient,
    a flow probe configured to measure a flow rate of said flow of gases through said breathing assistance system, and
    a controller configured to:
        receive data relating to said temperature of said flow of gases measured by said patient end temperature sensor, data relating to said flow rate measured by said flow probe, and data relating to said temperature measured by said ambient temperature sensor,
        determine a target patient end gases temperature based at least in part on said data relating to said flow rate measured by said flow probe and said data relating to said temperature measured by said ambient temperature sensor, wherein said target patient end gases temperature varies based on a change in at least one of said flow rate measured by said flow probe or said temperature measured by said ambient temperature sensor,
        compare said target patient end gases temperature to said temperature of said flow of gases measured by said patient end temperature sensor and determine, based on said comparison, a control output comprising a target heater wire power, and
        adjust power delivered to said heater wire to substantially match said heater wire power and to cause said temperature of said flow of gases measured by said patient end temperature sensor to substantially match said target patient end gases temperature,
    the controller further configured to: assess that said humidifier unit is experiencing high convective heat loss when said power delivered to said heater wire meets or exceeds a first preset threshold power level for a first preset time period, and adjust power delivered to said heater wire in response to a determination that said humidifier unit is experiencing high convective heat loss.

2. A breathing assistance system as claimed in claim 1, wherein said controller is configured to determine said control output further based at least in part on a rule-based system loaded in a memory of said controller.

3. A breathing assistance system as claimed in claim 1, wherein said controller is configured to determine said control output further based at least in part on at least one mathematical formula loaded in a memory of said controller.

4. A breathing assistance system as claimed in claim 1, wherein said controller is configured to determine said control output using further based at least in part on a look-up table loaded in a memory of said controller.

5. A breathing assistance system as claimed in claim 1, wherein said controller is further configured to adjust power delivered to at least said heater wire to achieve a user-set target dew point temperature.

6. A breathing assistance system as claimed in claim 5, wherein said user set target dew point temperature relates to an absolute humidity level of substantially 44 mg $H_2O$/liter of air.

7. A breathing assistance system as claimed in claim 1, wherein said ambient temperature sensor is located at or close to said inlet port and is configured to measure the temperature of said flow of gases substantially as it enters said humidifier unit.

8. A breathing assistance system as claimed in claim 1, further comprising an exit port temperature sensor configured to measure a temperature of said flow of gases substantially as it exits said humidifier unit, said controller further configured to receive data relating to said temperature measured by said exit port temperature sensor and to determine said control output further based at least in part on said data relating to said temperature measured by said exit port temperature sensor.

9. A breathing assistance system as claimed in claim 1, wherein said breathing assistance system further comprises a humidity sensor configured to measure humidity of atmospheric gases entering said breathing assistance system, said controller further configured to receive data relating to the measured humidity and determine said control output further based on said data relating to the measured humidity.

10. A breathing assistance system as claimed in claim 1, further comprising a pressure sensor configured to measure a pressure of atmospheric gases entering said breathing assistance system, said controller further configured to receive data relating to said pressure measured by said pressure sensor and to determine said control output further based at least in part on said data relating to said pressure measured by said pressure sensor.

11. A breathing assistance system as claimed in claim 1, further comprising a control unit located in a gases flow path between a central gases source and said humidifier unit, said control unit configured to receive said flow of gases and to deliver said flow of gases to said humidifier unit, said control unit comprising user controls configured to enable a user to set a desired user-set flow rate.

12. A breathing assistance system as claimed in claim 11, further comprising a venturi configured to mix said flow of gases with atmospheric gases before delivering said flow of gases to said humidifier unit.

13. A breathing assistance system as claimed in claim 1, further comprising a blower unit configured to be fluidically connected to said humidifier unit, said blower unit comprising an adjustable, variable speed fan unit configured to deliver said flow of gases over a range of flow rates to said humidifier unit, said blower unit further comprising user controls configured to enable a user to set a user-set flow rate, wherein said controller is further configured to adjust power delivered to at least said blower unit to produce said user-set flow rate.

14. A breathing assistance system as claimed in claim 1, wherein said first preset threshold power level and said first preset time period are stored in a memory of said controller.

15. A breathing assistance system as claimed in claim 1, wherein said humidifier unit further comprises:
a humidifier chamber configured to hold said volume of water,
a heater plate configured to heat said volume of water, and
a heater plate temperature sensor configured to measure a temperature of said heater plate,
wherein said controller is further configured to: receive data relating to said temperature measured by said heater plate temperature sensor and to adjust power delivered to at least said heater plate.

16. A breathing assistance system as claimed in claim 15, wherein said controller is further configured to: assess that said humidifier unit is experiencing high convective heat loss when said temperature measured by said heater plate temperature sensor meets or exceeds a second preset threshold temperature for a second preset time period, said second preset threshold temperature and said second preset time period being stored in the memory of said controller, and adjust power delivered to at least said heater plate in response to a determination that said humidifier unit is experiencing high convective heat loss.

17. A breathing assistance system as claimed in claim 1, further comprising an unheated secondary hose configured to fluidically connect a patient end of said conduit comprising said heater wire to said interface, wherein said patient end temperature sensor is located at or close to said patient end of the conduit comprising said heater wire.

18. A breathing assistance system as claimed in claim 1, wherein said controller is further configured to adjust the power delivered to said heater wire to maintain or alter said temperature of said flow of gases to achieve a desired patient end temperature and absolute humidity at said interface.

19. A breathing assistance system as claimed in claim 18, wherein said desired humidity is associated with a user-set target dew point temperature in the range 31-38° C.

20. A breathing assistance system as claimed in claim 1, wherein said adjustment in response to said determination that said humidifier unit is experiencing high convective heat loss comprises application of an inversely linear correction factor to said power delivered to said heater wire.

21. A breathing assistance system as claimed in claim 1, wherein said controller is configured to determine said target patient end gases temperature further based on pressure of said flow of gases before said flow of gases enters said humidifier unit.

* * * * *

UNITED STATES PATENT AND TRADEMARK OFFICE
CERTIFICATE OF CORRECTION

PATENT NO. : 10,058,663 B2
APPLICATION NO. : 14/092488
DATED : August 28, 2018
INVENTOR(S) : Stanislav Tatkov et al.

Page 1 of 2

It is certified that error appears in the above-identified patent and that said Letters Patent is hereby corrected as shown below:

On the Title Page

Item (71), Applicant Line 1, change "HEATHCARE" to --HEALTHCARE--

In the Specification

In Column 3, Line 27, change "A," to --A--

In Column 3, Line 55, change "tided:" to --titled:--

In Column 6, Line 14, change "$H_2 0$" to --$H_2O$--

In Column 9, Line 58, change "mote" to --more--

In Column 10, Line 63, change "System" to --system--

In Column 11, Line 39, change "similar)" to --similar).--

In Column 13, Line 28, change "unit." to --unit--

In Column 19, Line 35, change "(e g" to --(e.g.--

In Column 21, Line 66, change "low-draft'" to --'low-draft'--

In Column 22, Line 4, change "methods)" to --method(s)--

In Column 23, Line 5, change "then" to --than--

In Column 23, Line 39, change "power." to --power--

Signed and Sealed this
Eighteenth Day of June, 2019

Andrei Iancu
*Director of the United States Patent and Trademark Office*

CERTIFICATE OF CORRECTION (continued)
U.S. Pat. No. 10,058,663 B2

In Column 24, Line 44, change "m" to --in--

In Column 27, Line 23, change "algorithm." to -- algorithm--

In Column 27, Line 30, change "change)" to --change).--

In Column 27, Line 48, change "flares" to --nares--

In Column 28, Line 23, change "D'" to --'D'--

In the Claims

In Column 30, Line 29, Claim 1, change "a target heater" to --a heater--